United States Patent
Aikawa et al.

(10) Patent No.: US 12,378,307 B2
(45) Date of Patent: Aug. 5, 2025

(54) ANTIBODIES BLOCKING DLL4-MEDIATED NOTCH SIGNALLING

(71) Applicant: The Brigham and Women's Hospital, Inc., Boston, MA (US)

(72) Inventors: Masanori Aikawa, Chestnut Hill, MA (US); Toshiaki Nakano, Fukuoka (JP); Shunsuke Katsuki, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 1066 days.

(21) Appl. No.: 17/294,147

(22) PCT Filed: Nov. 14, 2019

(86) PCT No.: PCT/US2019/061534
§ 371 (c)(1),
(2) Date: May 14, 2021

(87) PCT Pub. No.: WO2020/102577
PCT Pub. Date: May 22, 2020

(65) Prior Publication Data
US 2022/0017610 A1      Jan. 20, 2022

Related U.S. Application Data

(60) Provisional application No. 62/768,848, filed on Nov. 16, 2018.

(51) Int. Cl.
*C07K 16/18*     (2006.01)
*G01N 33/563*    (2006.01)

(52) U.S. Cl.
CPC ........... *C07K 16/18* (2013.01); *G01N 33/563* (2013.01); *C07K 2317/24* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | |
|---|---|---|
| 6,180,370 B1 * | 1/2001 | Queen ..................... A61P 19/02 435/69.6 |
| 6,703,221 B1 | 3/2004 | Chan et al. |
| 8,133,857 B2 | 3/2012 | Aikawa |
| 8,889,131 B2 | 11/2014 | Aikawa et al. |
| 9,567,396 B2 | 2/2017 | Aikawa et al. |
| 2010/0292312 A1 | 11/2010 | Yan et al. |
| 2010/0303812 A1 | 12/2010 | Sunamura et al. |
| 2011/0262929 A1 | 10/2011 | Kawai et al. |
| 2014/0212423 A1 | 7/2014 | Hanzatian et al. |
| 2015/0183856 A1 | 7/2015 | Kim et al. |
| 2016/0031986 A1 | 2/2016 | Chen et al. |
| 2016/0130334 A1 | 5/2016 | Aikawa et al. |
| 2016/0176962 A1 * | 6/2016 | Murriel ................ A61K 31/519 424/139.1 |
| 2018/0230207 A1 | 8/2018 | Aikawa et al. |

OTHER PUBLICATIONS

Stryer, Biochemistry 4th, WH Freeman, New York. 1995 (Year: 1995).*
Colman, Peter M. Research in Immunology 145.1 (1994): 33-36 (Year: 1994).*
Nakano, Toshiaki, et al. Arteriosclerosis, thrombosis, and vascular biology 36.10 (2016): 2038-2047 (Year: 2016).*
Billiard, Fabienne, et al. Cell reports 22.4 (2018): 895-904 (Year: 2018).*
Zhou, X L, and J C Liu. "Role of Notch signaling in the mammalian heart." Brazilian journal of medical and biological research = Revista brasileira de pesquisas medicas e biologicas vol. 47,1 (2014): 1-10. doi:10.1590/1414-431X20133177 (Year: 2014).*
Macrae, Jennifer M et al. "Arteriovenous Access Failure, Stenosis, and Thrombosis." Canadian journal of kidney health and disease vol. 3 2054358116669126. Sep. 27, 2016, doi:10.1177/2054358116669126 (Year: 2016).*
Gurney, Austin, and Timothy Hoey. "Anti-DLL4, a cancer therapeutic with multiple mechanisms of action." Vascular cell vol. 3 18. Aug. 10, 2011, doi:10.1186/2045-824X-3-18 (Year: 2011).*
Tran, Ivy T et al. "Blockade of individual Notch ligands and receptors controls graft-versus-host disease." The Journal of clinical investigation vol. 123,4 (2013): 1590-604. doi:10.1172/JCI65477 (Year: 2013).*
Park, Jong-Sung, et al. "Inhibition of notch signalling ameliorates experimental inflammatory arthritis." Annals of the rheumatic diseases 74.1 (2015): 267-274 (Year: 2015).*
Zhang, Weijuan, Wei Xu, and Sidong Xiong. "Blockade of Notch1 signaling alleviates murine lupus via blunting macrophage activation and M2b polarization." The Journal of Immunology 184.11 (2010): 6465-6478 (Year: 2010).*
Dees, Clara et al. "Inhibition of Notch signaling prevents experimental fibrosis and induces regression of established fibrosis." Arthritis and rheumatism vol. 63,5 (2011): 1396-404. doi:10.1002/art.30254 (Year: 2011).*
Sohn, Sogu, et al. "Whole organ engineering: approaches, challenges, and future directions." Applied Sciences 10.12 (2020): 4277 (Year: 2020).*
Fukuda, Daiju, et al. "Notch ligand delta-like 4 blockade attenuates atherosclerosis and metabolic disorders." Proceedings of the national Academy of Sciences 109.27 (2012): E1868-E1877. (Year: 2012).*
Stone et al, "Glycogen Storage Disease", Treasure Island (FL): StatPearls Publishing; May 2023 (Year: 2023).*

(Continued)

*Primary Examiner* — Zachariah Lucas
*Assistant Examiner* — Lia E Taylor
(74) *Attorney, Agent, or Firm* — Fish & Richardson P.C.

(57) ABSTRACT

The present invention is directed to antibodies that interact with DLL4 and inhibit it from binding to NOTCH receptors. The invention also includes nucleic acids encoding the antibodies and methods of using the antibodies in research and in the prevention or treatment of various diseases and conditions.

23 Claims, 7 Drawing Sheets
Specification includes a Sequence Listing.

(56) References Cited

OTHER PUBLICATIONS

Stone et al, "Phenylketonuria", Treasure Island (FL): StatPearls Publishing; Aug. 2023 (Year: 2023).*
Wang, Yun et al. "Blocking Notch in endothelial cells prevents arteriovenous fistula failure despite CKD." Journal of the American Society of Nephrology : JASN vol. 25,4 (2014): W773-83. doi:10.1681/ASN.2013050490 (Year: 2014).*
Kipriyanov, Sergey M., and Fabrice Le Gall. "Generation and production of engineered antibodies." Molecular biotechnology 26.1 (2004): 39-60. (Year: 2004).*
Janeway, Charles A. "Immunobiology: The Immune System in Health and Disease." 2001 (Year: 2001).*
Billiard et al., "Delta-like ligand-4-notch signaling inhibition regulates pancreatic islet function and insulin secretion," Cell Reports, Jan. 23, 2018, 22(4):895-904.
Briot et al., "Blockade of specific Notch ligands: a new promising approach in cancer therapy," Cancer Discovery, Feb. 1, 2015, 5(2):112-4.
Brou et al., "A novel proteolytic cleavage involved in Notch signaling: the role of the disintegrin-metalloprotease TACE," Molecular Cell, Feb. 1, 2000, 5(2):207-16.
Brzozowa et al., "The Notch ligand Delta-like 4 (DLL4) as a target in angiogenesis-based cancer therapy?," Contemporary Oncology, Jun. 2013, 17(3):234.
De Strooper et al., "A presenilin-1-dependent γ-secretase-like protease mediates release of Notch intracellular domain," Nature, Apr. 1999, 398(6727):518-22.
Gurney et al., "Anti-DLL4, a cancer therapeutic with multiple mechanisms of action," Vascular Cell, Dec. 2011, 3(1):1-4.

Kang et al., "Concurrent Treatment with Anti-DLL4 Enhances Antitumor and Proapoptotic Efficacy of a γ-Secretase Inhibitor in Gastric Cancer," Translational Oncology, Jun. 1, 2018, 11(3):599-608.
Koga et al., "Macrophage notch ligand delta-like 4 promotes vein graft lesion development: implications for the treatment of vein graft failure," Arteriosclerosis, Thrombosis, and Vascular Biology, Nov. 2015, 35(11):2343-53.
Kuhnert et al., "Dll4-Notch signaling as a therapeutic target in tumor angiogenesis," Vascular Cell, Dec. 2011, 3(1):1-8.
Kuramoto et al., "Dll4-Fc, an inhibitor of Dll4-notch signaling, suppresses liver metastasis of small cell lung cancer cells through the downregulation of the NF-κB activity," Molecular Cancer Therapeutics, Dec. 1, 2012, 11(12):2578-87.
Mumm et al., "A ligand-induced extracellular cleavage regulates γ-secretase-like proteolytic activation of Notch1," Molecular Cell, Feb. 1, 2000, 5(2):197-206.
Nakano et al., "Delta-like ligand 4-notch signaling in macrophage activation," Arteriosclerosis, Thrombosis, and Vascular Biology, Oct. 2016, 36(10):2038-47.
Park et al., "Inhibition of notch signalling ameliorates experimental inflammatory arthritis," Annals of the Rheumatic Diseases, Jan. 1, 2015, 74(1):267-74.
PCT International Preliminary Report on Patentability in International Appln. No. PCT/US2019/061534, dated May 18, 2021, 7 pages.
PCT International Search Report and Written Opinion in International Appln. No. PCT/US2019/061534, dated Feb. 21, 2020, 9 pages.
Selkoe et al., "Notch and Presenilin: regulated intramembrane proteolysis links development and degeneration," Annual Review of Neuroscience, Mar. 2003, 26(1):565-97.

* cited by examiner

ANTIBODIES BLOCKING DLL4-MEDIATED NOTCH SIGNALLING

CLAIM OF PRIORITY

The present application is the U.S. National Phase Application under 35 U.S.C. § 371 of International Patent Application No. PCT/US2019/061534, filed on Nov. 14, 2019, which claims the benefit of U.S. Provisional Patent Application No. 62/768,848, filed on Nov. 16, 2018, which is hereby incorporated by reference in its entirety.

STATEMENT OF GOVERNMENT FUNDING

This invention was made with government support under NIH Grant No. R01HL107550, awarded by the Department of Health and Human Services. The government has certain rights in the invention.

SEQUENCE LISTING

This application contains a Sequence Listing that has been submitted electronically as an ASCII text file named 29618_0340US1_Sequence_Listing. The ASCII text filed, created on May 11, 2021, is 40.0 KB (40,960 bytes) in size. The material in the ASCII text file is hereby incorporated by reference in its entirety.

FIELD OF THE INVENTION

The present invention is concerned with agents that can be used to modify the NOTCH signaling pathway of cells. In particular, it is concerned with antibodies that inhibit DLL4-induced NOTCH activity and the use of these antibodies in research, as well as in the prevention and treatment of a variety of diseases or conditions.

BACKGROUND OF THE INVENTION

The NOTCH signaling pathway has been identified as playing an important role in many diverse biological functions, including differentiation and cellular proliferation (see U.S. Pat. No. 6,703,221). The pathway is activated by four different transmembrane receptor subtypes (designated as NOTCH-1-NOTCH-4) that have both an extracellular and intracellular domain (Nakano, et al., *Atheroscl. Thromb. & Vascul. Biol.* 36:2038-2047 (August 2016)). The extracellular portion of the receptors binds to ligands of the Jagged (Jagged1, Jagged2) and Delta-like (DLL1, DLL3, DLL4) families found on the surfaces of other cells. Following ligand binding, the receptor undergoes sequential cleavage by metalloproteases of the ADAM family (Bru, et al., *Mol. Cell* 5:207-216 (2000); Mumm, et al., *Mol. Cell* 5:197-206 (2000)) and the presenilin-dependent gamma-secretase (Selkoe, et al., *Annu. Rev. Neurosci.* 26:565-97 (2003); De Strooper, et al., *Nature* 398:518-522 (1999)). The final proteolytic cleavage step permits the intracellular domain of the NOTCH receptor to translocate to the cell nucleus where it interacts with transcription factors to induce target gene expression.

Over the last several years, evidence has accumulated that suggests that DLL4-mediated NOTCH signaling contributes to proinflammatory macrophage activation and to associated cardiovascular diseases, including atherosclerosis and vascular calcification (U.S. Pat. No. 8,133,857; Nakano, et al., *Atheroscl. Thromb. & Vascul. Biol.* 36:2038-2047 (August 2016), Nakano, et al., *Circulation*, in press). In addition, inhibition of DLL4-induced NOTCH activation has been associated with: vein graft disease (U.S. Pat. No. 9,567,396; Koga, et al. *Atheroscl. Thromb. & Vascul. Biol.* 35:2343-2353 (November 2015)); nonalcoholic fatty liver disease (US 2018/0230207); obesity (US 2016/0130334); metabolic disease (U.S. Pat. No. 8,889,131); type 1 and type 2 diabetes (Billiard, et al.; *Cell Reports* 22:895-904 (January 2018); cancer, including colorectal, breast and lung cancer (Gurney, et al., *Vascular. Cell.* 3:18 (2011); Kuhnert, et al., *Vascular Cell.* 3:20 (2011); Brzozowa, et al., *Contemp. Oncol.* 17:234-237 (2013); Kang, et al., *Transl. Oncol.* 11:599-608 (June 2018); Briot, et al.; *Cancer Discov.* 5:112-114 (February 2015)); tumor cell metastasis (Kuramoto, et al., *Mol. Cancer Ther.* 11(12):2578-2587 (December 2012)); and arthritis (Park, et al., *Ann. Rheum. Dis.* 2013; 0:1-8. doi: 10.1136/annrheumdis-2013-203467)).

Because of their substantial therapeutic potential, inhibitors of DLL4 signaling, and especially inhibitors that are relatively specific in their action, are of great interest.

SUMMARY OF THE INVENTION

The present invention is based on the development of monoclonal antibodies that bind with high affinity to human DLL4 and that may be used to inhibit NOTCH receptor binding and NOTCH pathway activation. In some cases, the antibodies also have little or no effect on human DLL1. Thus, they may be used in research to help differentiate the effect of these NOTCH ligands and in patients without interfering with the normal biological action of DLL1. The antibodies also cross react with porcine DLL4.

The tables below are directed to six IgG type monoclonal antibodies that bind to DLL4 and that are structurally characterized with respect to light and heavy chain variable regions (and particularly complementarity determining regions (HCDRs and LCDRs) and framework regions (HFRs and LFRs) responsible for recognizing and interacting with this ligand. In some cases, information regarding an association rate constant (ka, in $M^{-1}s^{-1}$) and a dissociation rate constant (kd, in $s^{-1}$) for human DLL4 is provided either in the Table or a later description. These constants are for assays performed in 10 mM HEPES buffer (pH 7.4), 150 mM NaCl, 3 mM EDTA, 0.05% P20 (poly oxy ethylenesorbitan).

The present invention includes all antibodies with any combination of elements recited in a single table or in different tables. For example, the invention includes all combinations of light and heavy chain variable regions (and particularly complementarity determining regions (HCDRs and LCDRs) and framework regions (HFRs and LFRs) shown in the tables. Preferably the antibodies are IgG antibodies (especially monoclonal antibodies), that bind to human DLL4 with an affinity at least 1000 times (and preferably at least 10,000 or 100,000 times) higher than to human DLL1.

TABLE 1

Monoclonal Antibody 2H10
(little or no binding to human DLL1)

| Region | Nucleotides Source: SEQ ID NO: 1 | Amino Acids Source: SEQ ID NO: 2 |
| --- | --- | --- |
| Heavy chain variable region | 31-390 | 1-120 |
| HFR1-2H10 | 31-120 | 1-30 |
| HCDR1-2H10 | 121-135 | 31-35 |

TABLE 1-continued

Monoclonal Antibody 2H10
(little or no binding to human DLL1)

| Region | | |
|---|---|---|
| HFR2-2H10 | 136-177 | 36-49 |
| HCDR2-2H10 | 178-225 | 50-65 |
| HFR3-2H10 | 226-321 | 66-97 |
| HCDR3-2H10 | 322-363 | 98-111 |
| HFR4-2H10 | 364-390 | 112-120 |

| Region | Nucleotides Source: SEQ ID NO: 3 | Amino Acids Source: SEQ ID NO: 4 |
|---|---|---|
| Light chain variable region | 3-311 | 1-103 |
| LFR1-2H10 | 3-53 | 1-17 |
| LCDR1-2H10 | 54-86 | 18-28 |
| LFR2-2H10 | 87-131 | 29-43 |
| LCDR2-2H10 | 132-152 | 44-50 |
| LFR3-2H10 | 153-248 | 51-83 |
| LCDR3-2H10 | 249-275 | 84-91 |
| LFR4-2H10 | 276-311 | 92-103 |

TABLE 2

Monoclonal Antibody 5D7

| Region | Nucleotides Source: SEQ ID NO: 5 | Amino Acids Source: SEQ ID NO: 6 |
|---|---|---|
| Heavy chain variable region | 55-414 | 1-120 |
| HFR1-5D7 | 55-144 | 1-30 |
| HCDR1-5D7 | 145-159 | 31-35 |
| HFR2-5D7 | 160-201 | 36-49 |
| HCDR2-5D7 | 202-249 | 50-65 |
| HFR3-5D7 | 250-345 | 66-97 |
| HCDR3-5D7 | 346-381 | 98-109 |
| HFR4-5D7 | 382-414 | 110-120 |

| Region | Nucleotides Source: SEQ ID NO: 7 | Amino Acids Source: SEQ ID NO: 8 |
|---|---|---|
| Light chain variable region | 23-352 | 1-110 |
| LFR1-5D7 | 23-88 | 1-22 |
| LCDR1-5D7 | 89-133 | 23-37 |
| LFR2-5D7 | 134-178 | 38-52 |
| LCDR2-5D7 | 179-199 | 53-59 |
| LFR3-5D7 | 200-295 | 60-91 |
| LCDR3-5D7 | 296-322 | 92-100 |
| LFR4-5D7 | 323-352 | 101-110 |

TABLE 3

Monoclonal Antibody 8B2

| Region | Nucleotides Source: SEQ ID NO: 9 | Amino Acids Source: SEQ ID NO: 10 |
|---|---|---|
| Heavy chain variable region | 1-342 | 1-114 |
| HFR1-8B2 | 1-57 | 1-19 |
| HCDR1-8B2 | 58-87 | 20-29 |
| HFR2-8B2 | 88-129 | 30-43 |
| HCDR2-8B2 | 130-159 | 44-53 |
| HFR3-8B2 | 160-276 | 54-92 |
| HCDR3-8B2 | 277-309 | 93-103 |
| HFR4-8B2 | 310-342 | 104-114 |

TABLE 3-continued

Monoclonal Antibody 8B2

| Region | Nucleotides Source: SEQ ID NO: 11 | Amino Acids Source: SEQ ID NO: 12 |
|---|---|---|
| Light chain variable region | 141-461 | 1-107 |
| LFR1-8B2 | 141-209 | 1-23 |
| LCDR1-8B2 | 210-242 | 24-34 |
| LFR2-8B2 | 243-287 | 35-49 |
| LCDR2-8B2 | 288-308 | 50-56 |
| LFR3-8B2 | 309-404 | 57-88 |
| LCDR3-8B2 | 405-431 | 89-97 |
| LFR4-8B2 | 432-461 | 98-107 |

TABLE 4

Monoclonal Antibody 8C2
For human DLL4, ka greater than $5.0 \times 10^5$; kd less than $5.0 \times 10^{-3}$
(little or no binding to human DLL1)

| Region | Nucleotides Source: SEQ ID NO: 13 | Amino Acids Source: SEQ ID NO: 14 |
|---|---|---|
| Heavy chain variable region | 33-374 | 1-114 |
| HFR1-8C2 | 33-122 | 1-30 |
| HCDR1-8C2 | 123-137 | 31-35 |
| HFR2-8C2 | 138-179 | 36-49 |
| HCDR2-8C2 | 180-227 | 50-65 |
| HFR3-8C2 | 228-317 | 66-95 |
| HCDR3-8C2 | 318-341 | 96-103 |
| HFR4-8C2 | 342-374 | 104-114 |

| Region | Nucleotides Source: SEQ ID NO: 15 | Amino Acids Source: SEQ ID NO: 16 |
|---|---|---|
| Light chain variable region | 1-318 | 1-106 |
| LFR1-8C2 | 1-69 | 1-23 |
| LCDR1-8C2 | 70-102 | 24-34 |
| LFR2-8C2 | 103-147 | 35-49 |
| LCDR2-8C2 | 148-168 | 50-56 |
| LFR3-8C2 | 169-264 | 57-88 |
| LCDR3-8C2 | 265-291 | 89-97 |
| LFR4-8C2 | 292-318 | 98-106 |

TABLE 5

Monoclonal Antibody 8D2
For human DLL4, ka greater than $1.0 \times 10^5$; kd less than $5.0 \times 10^{-3}$
(little or no binding to human DLL1)

| Region | Nucleotides Source: SEQ ID NO: 17 | Amino Acids Source: SEQ ID NO: 18 |
|---|---|---|
| Heavy chain variable region | 1-345 | 1-115 |
| HFR1-8D2 | 1-72 | 1-24 |
| HCDR1-8D2 | 73-87 | 25-29 |
| HFR2-8D2 | 88-129 | 30-43 |
| HCDR2-8D2 | 130-180 | 44-60 |
| HFR3-8D2 | 181-276 | 61-92 |
| HCDR3-8D2 | 277-312 | 93-104 |
| HFR4-8D2 | 313-345 | 105-110 |

TABLE 5-continued

Monoclonal Antibody 8D2
For human DLL4, ka greater than $1.0 \times 10^5$; kd less than $5.0 \times 10^{-3}$
(little or no binding to human DLL1)

| Region | Nucleotides Source: SEQ ID NO: 19 | Amino Acids Source: SEQ ID NO: 20 |
|---|---|---|
| Light chain variable region | 36-365 | 1-110 |
| LFR1-8D2 | 36-101 | 1-22 |
| LCDR1-8D2 | 102-146 | 23-37 |
| LFR2-8D2 | 147-191 | 38-52 |
| LCDR2-8D2 | 192-212 | 53-59 |
| LFR3-8D2 | 213-308 | 60-91 |
| LCDR3-8D2 | 309-335 | 92-100 |
| LFR4-8D2 | 336-365 | 101-110 |

TABLE 6

Monoclonal Antibody 10C5

| Region | Nucleotides Source: SEQ ID NO: 21 | Amino Acids Source: SEQ ID NO: 22 |
|---|---|---|
| Light chain variable region | 1-306 | 1-102 |
| LFR1-10C5 | 1-54 | 1-18 |
| LCDR1-10C5 | 55-87 | 19-29 |
| LFR2-10C5 | 88-132 | 30-44 |
| LCDR2-10C5 | 133-153 | 45-51 |
| LFR3-10C5 | 154-249 | 52-83 |
| LCDR3-10C5 | 250-276 | 84-92 |
| LFR4-10C5 | 277-306 | 93-102 |

The invention is directed, in part, to any IgG type antibodies or fragments thereof, especially monoclonal antibodies, with characteristics similar to those in the above tables. Specifically, the invention includes the following:

A. Antibodies with Characteristics Based on Table 4

The invention includes any IgG antibodies, or antibody fragments, preferably monoclonal antibodies or fragments, that bind to human DLL4 with an affinity at least 1000 times (and preferably at least 10,000 or 100,000 times) higher than to human DLL1, and that comprise: a) a heavy chain variable region at least 90% (and preferably 95% or 98%) identical to the sequence of amino acids 1-114 of SEQ ID NO:14 and/or which includes one or more heavy chain complementarity determining regions (HCDRs) selected from the group consisting of: HCDR1-8C2, amino acids 31-35 of SEQ ID NO:14; HCDR2-8C2, amino acids 50-65 of SEQ ID NO:14; and HCDR3-8C2, amino acids 96-103 of SEQ ID NO:14; and b) a light chain variable region at least 90% (and preferably 95% or 98%) identical to the sequence of amino acids 1-106 of SEQ ID NO:16 and/or which includes one or more light chain complementarity determining regions (LCDRs) selected from the group consisting of: LCDR1-8C2, amino acids 23-34 of SEQ ID NO:16; LCDR2-8C2, amino acids 50-56 of SEQ ID NO:16; and LCDR3-8C2, amino acids 89-97 of SEQ ID NO:16.

In a preferred embodiment, antibodies or antibody fragments have a heavy chain variable region comprising HCDR1-8C2, HCDR2-8C2, and HCDR3-8C2 and a light chain variable region comprising LCDR1-8C2, LCDR2-8C2, and LCDR3-8C2. In addition, the heavy and light chain variable regions may include any or all of the framework sequences described in Table 4.

The invention also includes nucleic acids encoding the antibodies, or antibody fragments, that, preferably, have a heavy chain variable region encoded by nucleotides 33-374 of SEQ ID NO:13 and a light chain variable region encoded by nucleotides 1-318 of SEQ ID NO:15. Preferred nucleic acid sequences encoding heavy chain CDRs are: for HCDR1-8C2, nucleotides 123-137 of SEQ ID NO:13; for HCDR2-8C2 nucleotides 180-227 of SEQ ID NO:13; and for HCDR3-8C2 nucleotides 318-341 of SEQ ID NO:13. Preferred nucleic acid sequences encoding light chain CDRs are: for LCDR1-8C2, nucleotides 70-102 of SEQ ID NO:15; for LCDR2-8C2, nucleotides 148-168 of SEQ ID NO:15; and for LCDR3-8C2, nucleotides 265-291 of SEQ ID NO:15.

B. Antibodies with Characteristics Based on Table 5

In a second aspect, the invention includes any IgG antibodies or antibody fragments, preferably monoclonal antibodies or fragments, that bind to human DLL4 with an affinity at least 1000 times (and preferably at least 10,000 or 100,000 times) higher than to human DLL1, and that comprise: a) a heavy chain variable region at least 90% (and preferably 95% or 98%) identical to the sequence of amino acids 1-115 of SEQ ID NO:18 and/or which includes one or more HCDRs selected from the group consisting of: HCDR1-8D2, amino acids 25-29 of SEQ ID NO:18; HCDR2-8D2, amino acids 44-60 of SEQ ID NO:18; and HCDR3-8D2, amino acids 93-104 of SEQ ID NO:18; and b) a light chain variable region at least 90% (and preferably 95% or 98%) identical to the sequence of amino acids 1-110 of SEQ ID NO:20 and/or which includes one or more LCDRs selected from the group consisting of: LCDR1-8D2, amino acids 23-37 of SEQ ID NO:20; LCDR2-8D2, amino acids 53-59 of SEQ ID NO:20; and LCDR3-8D2, amino acids 92-100 of SEQ ID NO:20.

In a preferred embodiment, antibodies, or antibody fragments, have a heavy chain variable region comprising: HCDR1-8D2; HCDR2-8D2; and HCDR3-8D2; and a light chain variable region comprising: LCDR1-8D2; LCDR2-8D2; and LCDR3-8D2. In addition, the heavy and light chain variable regions may include any or all of the framework sequences described in Table 5.

The invention also includes nucleic acids encoding the antibodies, or antibody fragments, that have a heavy chain variable region encoded by nucleotides 1-345 of SEQ ID NO:17 and a light chain variable region encoded by nucleotides 36-365 SEQ ID NO:19. Preferred nucleic acid sequences encoding heavy chain CDRs are: for HCDR1-8D2 nucleotides 73-87 of SEQ ID NO:17; for HCDR2-8D2, nucleotides 130-180 of SEQ ID NO:17; and for HCDR3-8D2, nucleotides 277-312 of SEQ ID NO:17. Preferred nucleic acid sequences encoding light chain CDRs are: for LCDR1-8D2, nucleotides 102-146 of SEQ ID NO:19; for LCDR2-8D2 nucleotides 192-212 of SEQ ID NO:19; and for LCDR3-8D2 nucleotides or 309-335 of SEQ ID NO:19.

C. Antibodies with Characteristics Based on Table 1

In a third aspect, the invention includes any IgG antibodies or antibody fragments, preferably monoclonal antibodies or fragments, that bind to human DLL4 with an affinity at least 1000 times (and preferably at least 10,000 or 100,000 times) higher than human DLL1, and that comprise: a) a heavy chain variable region at least 90% (and preferably 95% or 98%) identical to the sequence of amino acids 1-120 of SEQ ID NO:2 and/or which includes one or more HCDRs selected from the group consisting of: HCDR1-2H10, amino acids 31-35 of SEQ ID NO:2; HCDR2-2H10, amino acids 50-65 of SEQ ID NO:2; and HCDR3-2H10, amino acids 98-111 of SEQ ID NO:2; and a light chain variable region at least 90% identical to the sequence of amino acids 1-103 of SEQ ID NO:4 and/or which includes one or more LCDRs selected from the group consisting of LCDR1-2H10, amino acids 18-28 of SEQ ID NO:4; LCDR2-2H10, amino acids 44-50 of SEQ ID NO:4; and LCDR3-2H10, amino acids 84-91 of SEQ ID NO: 4.

In a preferred embodiment, antibodies or antibody fragments, have a heavy chain variable region comprising: HCDR1-2H10; HCDR2-2H10; and HCDR3-2H10; and a light chain variable region comprising: LCDR1-2H10; LCDR2-2H10; and LCDR3-2H10. In addition, the heavy and light chain variable regions may include any or all of the framework sequences described in Table 1.

The invention also includes nucleic acids encoding the antibodies, or antibody fragments, that have a heavy chain variable region preferably encoded by nucleotides 31-390 of SEQ ID NO:1 and a light chain variable region preferably encoded by nucleotides 3-311 of SEQ ID NO:3. Preferred nucleic acid sequences encoding heavy chain CDRs are: for HCDR1-2H10, nucleotides 121-135 of SEQ ID NO:1; for HCDR2-2H10, nucleotides 178-225 of SEQ ID NO:1; and for HCDR3-2H10, nucleotides 322-363 of SEQ ID NO:1. Preferred nucleic acid sequences encoding light chain CDRs are: for LCDR1-2H10, nucleotides 54-86 of SEQ ID NO:3; for LCDR2-2H10, nucleotides 132-152 of SEQ ID NO:3; and for LCDR3-2H10, nucleotides 249-275 of SEQ ID NO:3.

D. Antibodies with Characteristics Based on Table 2

In a fourth aspect, the invention includes any IgG antibodies or antibody fragments, preferably monoclonal antibodies or fragments, that bind to human DLL4 and which comprise: a) a heavy chain variable region at least 90% identical to the sequence of amino acids 1-120 of SEQ ID NO:6 and/or which includes one or more HCDRs selected from the group consisting of HCDR1-5D7, amino acids 31-35 of SEQ ID NO:6; HCDR2-5D7, amino acids 50-65 of SEQ ID NO:6; and HCDR3-5D7, amino acids 98-109 of SEQ ID NO:6; and b) a light chain variable region at least 90% identical to the sequence of amino acids 1-110 of SEQ ID NO:8 and/or which includes one or more LCDRs selected from the group consisting of: LCDR1-5D7, amino acids 23-37 of SEQ ID NO:8; LCDR2-5D7, amino acids 53-59 of SEQ ID NO:8; and LCDR3-5D7, amino acids 92-100 of SEQ ID NO:8.

In a preferred embodiment, antibodies or antibody fragments have a heavy chain variable region comprising: HCDR1-5D7; HCDR2-5D7; and HCDR3-5D7; and a light chain variable region comprising: LCDR1-5D7; LCDR2-5D7; and LCDR3-5D7. In addition, the heavy and light chain variable regions may include any or all of the framework sequences described in Table 2.

The invention also includes nucleic acids encoding the antibodies, or antibody fragments, that have a heavy chain variable region encoded by nucleotides 55-414 of SEQ ID NO:5 and a light chain variable region encoded by nucleotides 23-352 SEQ ID NO:7. Preferred nucleic acid sequences encoding heavy chain CDRs are: for HCDR1-5D7, nucleotides 145-159 of SEQ ID NO:5; for HCDR2-5D7, nucleotides 202-249 of SEQ ID NO:5; and for HCDR3-5D7, nucleotides 346-381 of SEQ ID NO:5. Preferred nucleic acid sequences encoding light chain CDRs are: for LCDR1-5D7, nucleotides 89-133 of SEQ ID NO:7; for LCDR2-5D7, nucleotides 179-199 of SEQ ID NO:7; and for LCDR3-5D7, nucleotides 296-322 of SEQ ID NO:7.

E. Antibodies with Characteristics Based on Table 3

In a fifth aspect, the invention includes any IgG antibodies or antibody fragments, preferably monoclonal antibodies or fragments, that bind to human DLL4 and that comprise: a) a heavy chain variable region at least 90% identical to the sequence of amino acids 1-114 of SEQ ID NO:10 and/or which includes one or more HCDRs selected from the group consisting of HCDR1-8B2, amino acids 20-29 of SEQ ID NO:10; HCDR2-8B2, amino acids 44-53 of SEQ ID NO:10; and HCDR3-8B2, amino acids 93-103 of SEQ ID NO:10; and b) a light chain variable region at least 90% identical to the sequence of amino acids 1-107 of SEQ ID NO:12 and/or which includes one or more LCDRs selected from the group consisting of LCDR1-8B2, amino acids 24-34 of SEQ ID NO:12; LCDR2-8B2, amino acids 50-56 of SEQ ID NO:12; and LCDR3-8B2, amino acids 89-97 of SEQ ID NO:12.

In a preferred embodiment, antibodies or antibody fragments, have a heavy chain variable region that comprises: HCDR1-8B2; HCDR2-8B2; and HCDR3-8B2; and the light chain variable region that comprises: LCDR1-8B2; LCDR2-8B2; and LCDR3-8B2. In addition, the heavy and light chain variable regions may include any or all of the framework sequences described in Table 3.

The invention also includes nucleic acids encoding the antibodies, or antibody fragments, that have a heavy chain variable region encoded by nucleotides 1-342 of SEQ ID NO:9 and a light chain variable region encoded by nucleotides 141-461 SEQ ID NO:11. Preferred nucleic acid sequences encoding heavy chain CDRs are: for HCDR1-8B2, nucleotides 58-87 of SEQ ID NO:9; for HCDR2-8B2, nucleotides 130-159 of SEQ ID NO:9; and for HCDR3-8B2, nucleotides 277-309 of SEQ ID NO:9. Preferred nucleic acid sequences encoding light chain CDRs are: for LCDR1-8B2, nucleotides 210-242 of SEQ ID NO:11; for LCDR2-8B2, nucleotides 288-308 of SEQ ID NO:11 and for LCDR3-8B2, nucleotides or 405-431 of SEQ ID NO:11.

F. Antibodies with Characteristics Based on Table 6

In a sixth aspect, the invention includes any IgG antibodies or antibody fragments, preferably monoclonal antibodies or fragments, that bind to human DLL4 and that comprise: a light chain variable region at least 90% identical to the sequence of amino acids 1-102 of SEQ ID NO:22 and/or which includes one or more LCDRs selected from the group consisting of LCDR1-10C5, amino acids 19-29 of SEQ ID NO:22; LCDR2-10C5, amino acids 45-51 of SEQ ID NO:22; and LCDR3-10C5, amino acids 84-92 of SEQ ID NO:22.

In a preferred embodiment, antibodies or antibody fragments have a light chain variable region that comprises: LCDR1-10C5, LCDR2-10C5, and LCDR3-10C5. In addition, the light chain variable region may include any or all of the framework sequences described in Table 6.

The invention also includes nucleic acids encoding the antibodies or antibody fragments that have a light chain variable region encoded by nucleotides 1-306 SEQ ID NO:21. Preferred nucleic acid sequences encoding light chain CDRs are: for LCDR1-10C5 nucleotides 55-87 of SEQ ID NO:21; for LCDR2-10C5, nucleotides 133-153 of SEQ ID NO:21; and for LCDR3-10C5, nucleotides 250-276 of SEQ ID NO:21.

G. Common Characteristics and Therapeutic Uses of Antibodies

All of the antibodies or antibody fragments described above (preferably monoclonal antibodies or fragments) should have an association rate constant, ka (1/Ms), for human DLL4 of $1.0\times10^4$ or higher (preferably $5.0\times10^4$ or higher and more preferably $1\times10^5$ or higher) and a dissociation rate constant, kd (1/s) of $5\times10^{-3}$ or less (and preferably $1.0\times10^{-3}$ or less).

Monoclonal antibodies may be nonhuman (e.g., mouse or rat antibodies), chimeric, humanized or fully human. Any of these different types of antibodies may be used for research purposes but humanized monoclonal antibodies (in which mouse CDR and, optionally also FR, regions replace the corresponding sites in human antibodies) or fully human monoclonal antibodies are preferred for use therapeutically in people, with fully human monoclonals being most preferred. Similarly, humanized or fully human antibody fragments (as opposed, for example, to nonhuman antibody fragments) are preferred for the treatment of human patients.

The antibodies or fragments of the antibodies may be modified to include any of the post-translational modifications that are known in the art and commonly applied to antibodies, provided that the modified antibodies or fragments maintain specificity for binding to human or porcine DLL4. Modifications may include PEGylation, phosphorylation, methylation, acetylation, ubiquitination, nitrosylation, glycosylation, ADP-ribosylation, or lipidation. Alternatively, or in addition, the antibodies or fragments may further comprise a detectable label that can be used to detect binding in an immunoassay. Labels that may be used include radioactive labels, fluorophores, chemiluminescent labels, enzymatic labels (e.g., alkaline phosphatase or horseradish peroxidase); biotin; avidin; and heavy metals.

The antibodies or fragments may be used in the treatment or prevention of diseases or conditions in humans that are caused or exacerbated by the binding of DLL4 to NOTCH receptors. Typically, this will involve administering a therapeutically effective amount of the antibody systemically or locally to a patient. The antibody is preferably administered by injection as part of a pharmaceutical composition that also includes a pharmaceutically acceptable carrier. Other active agents or excipients may also be included in the compositions administered. Diseases or conditions that may be treated or prevented include: cardiovascular disease, including atherogenesis, atherosclerosis and vascular calcification; vein graft disease; nonalcoholic fatty liver disease; obesity; metabolic disease; type 1 and type 2 diabetes; cancer, including colorectal, breast and lung cancer; tumor cell metastasis; arthritis; autoimmune diseases such as rheumatoid arthritis, scleroderma, and systemic lupus erythematosus; failure or dysfunction of artificial or tissue-engineered tissues or organs; and rejection or graft-versus-host disease after organ or cell transplantation.

H. Use in Assays

The antibodies or antibody fragments described herein may be used to bind to DLL4 (preferably human or porcine DLL4) as part of any of the immunoassays that are commonly used in the art. In some assays (typically called "one step" or "direct" assays) the antibodies or fragments will include a detectable label such as a radioactive label, fluorophore, chemiluminescent label, or enzymatic label. In other assays (typically called "two step" or "indirect" assays), the unlabeled antibody or fragment will constitute a "first" antibody and will bind to DLL4. Then a "second" antibody that has a detectable label will be used to bind to the first antibody. In a variation of a two step assay, the first antibody or fragment will include a binding agent such as biotin and then bind to a complementary binding agent, e.g. avidin, that is, or has been modified to be, detectable. Many variations on these assays have been described in the art and can be used. Examples of specific types of immunoassays include immunohistochemistry, Western blots, fluorescence-activated cell sorting, chemiluminescence immunoassays, radioimmunoassays, enzyme linked immunosorbent assays, immunoprecipitation assays, and immunoelectron microscopy.

In a preferred assay, DLL4-expressing cells in a test sample from a subject may be detected or quantitated by assaying the sample for cells expressing DLL4 using one of the assays discussed above. The test sample may be a bodily fluid (e.g., blood, plasma or serum) or it may be a tissue or cell sample obtained, for example, by biopsy or autopsy. The subject may be a laboratory animal or a human and may either be normal (i.e., disease free) or have a disease or condition selected from the group consisting of: cardiovascular disease; vein graft disease; arteriovenous fistula failure; nonalcoholic fatty liver disease; obesity; metabolic disease; type 1 or type 2 diabetes; cancer; and transplanted tissues or organs.

I. Use as Research Tools Apart from being used therapeutically and in the assays discussed above, the antibodies or antibody fragments described herein may be used by researchers studying the effects of DLL-4. For example, antibodies might be administered to test animals during development to help determine the effect that DLL4-mediated NOTCH pathway activation has on this process. Studies might be also be used to examine DLL4's contribution to disease processes or to look at effects on the activities of specific types of cells.

BRIEF DESCRIPTION OF THE DRAWINGS

FIGS. 1A and 1B show the results from experiments in which DLL4-expressing Cf2Th cells were combined with control IgG or serum, followed by recombinant NOTCH1-Fc and PE anti-IgG Fc. In FIG. 1B, results are merged from three independent determinations.

FIG. 2 shows the results of three experiments in which DLL4 binding assays (using supernatants) were performed.

FIGS. 3A and 3B show the result of DLL4 binding assays performed using purified antibodies and Cf2Th cells. The DLL4-expressing Cf2Th cells were added with neutralizing DLL4 antibodies (or control IgG), followed by recombinant NOTCH1-Fc and PE anti-IgG Fc. The results shown in FIG. 3B are based on three independent experiments.

FIGS. 4A and 4B show the results of a DLL4 binding assay performed using purified antibodies and HEK293T cells. The DLL4-expressing HEK293T cells were added with neutralizing DLL4 antibodies (or control IgG), followed by recombinant NOTCH1-Fc and PE anti-IgG Fc. The results shown in FIG. 4B are based on three independent experiments.

FIG. 5 shows the results of an RBP-Jx reporter assay. RBP-JK is a key transcription factor of the pan NOTCH pathway. NOTCH signaling activates RBP-Jx. Recombinant human DLL4 was coated on the culture plates ("immobilized DLL4"). Neutralizing DLL4 antibodies or control IgG were added in the medium. The RBP-Jx reporter construct was transfected in the mouse macrophage cell line RAW264.7. RAW264.7 cells were then seeded on culture plates coated with recombinant DLL4. After 48 hours. The relative luciferase values (RPB-JK firefly luciferase/control CMV *Renilla* luciferase) were measured. The results shown are based on three independent experiments.

FIG. 6 was part of a study examining whether the monoclonal antibodies 8D2 and 8C2 recognize the same, or overlapping, epitopes on either human or porcine DLL4. In the figure shown, the surface of a Biacore chip was coated with human DLL4 and the monoclonal antibody 8D2 was then allowed to bind to the immobilized DLL4 until all binding sites appeared to be saturated. The chip was then exposed to the monoclonal antibody 8C2 while measuring changes in surface plasmon resonance.

FIG. 7 shows the sensor readings obtained from an experiment similar to that described in FIG. 6 except that porcine DLL4 was used to coat the surface of the Biacore chip instead of human DLL4.

FIG. 8 shows the results of an experiment that is essentially the same as that described in FIG. 6, except that the order of addition of 8D2 and 8C2 was reversed, i.e., 8C2 was bound to immobilized human DLL4 and 8D2 was then introduced.

FIG. 9 shows the results of an experiment that is essentially the same as that described in FIG. 7, except that the order of addition of 8D2 and 8C2 was reversed, i.e., 8C2 was bound to immobilized porcine DLL4 and 8D2 was then introduced.

DETAILED DESCRIPTION OF THE INVENTION

A. Definitions

Figure 1A:
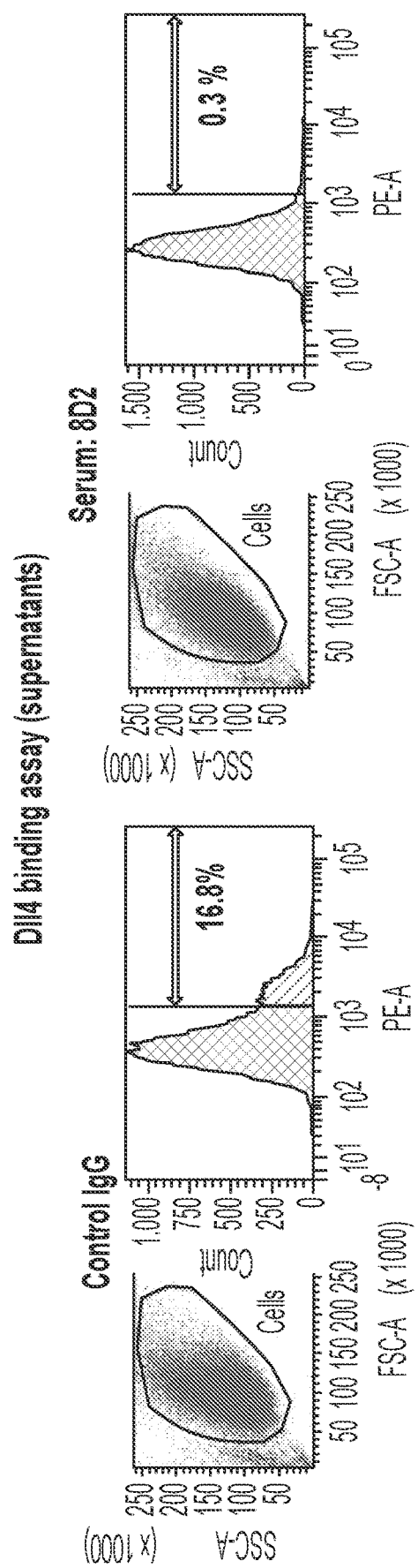
FIGS. 1A and 1B.
Figure 1B:
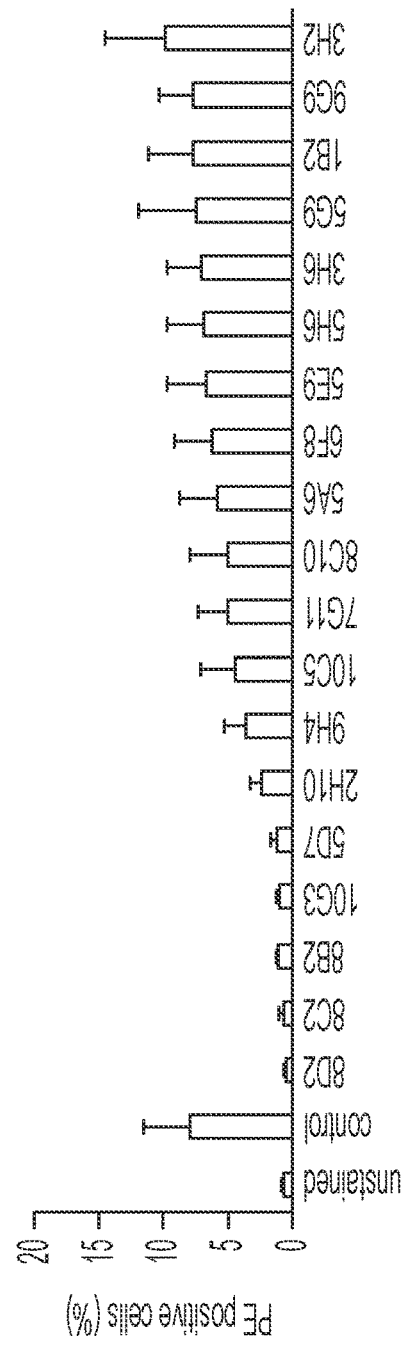
Figure 2:
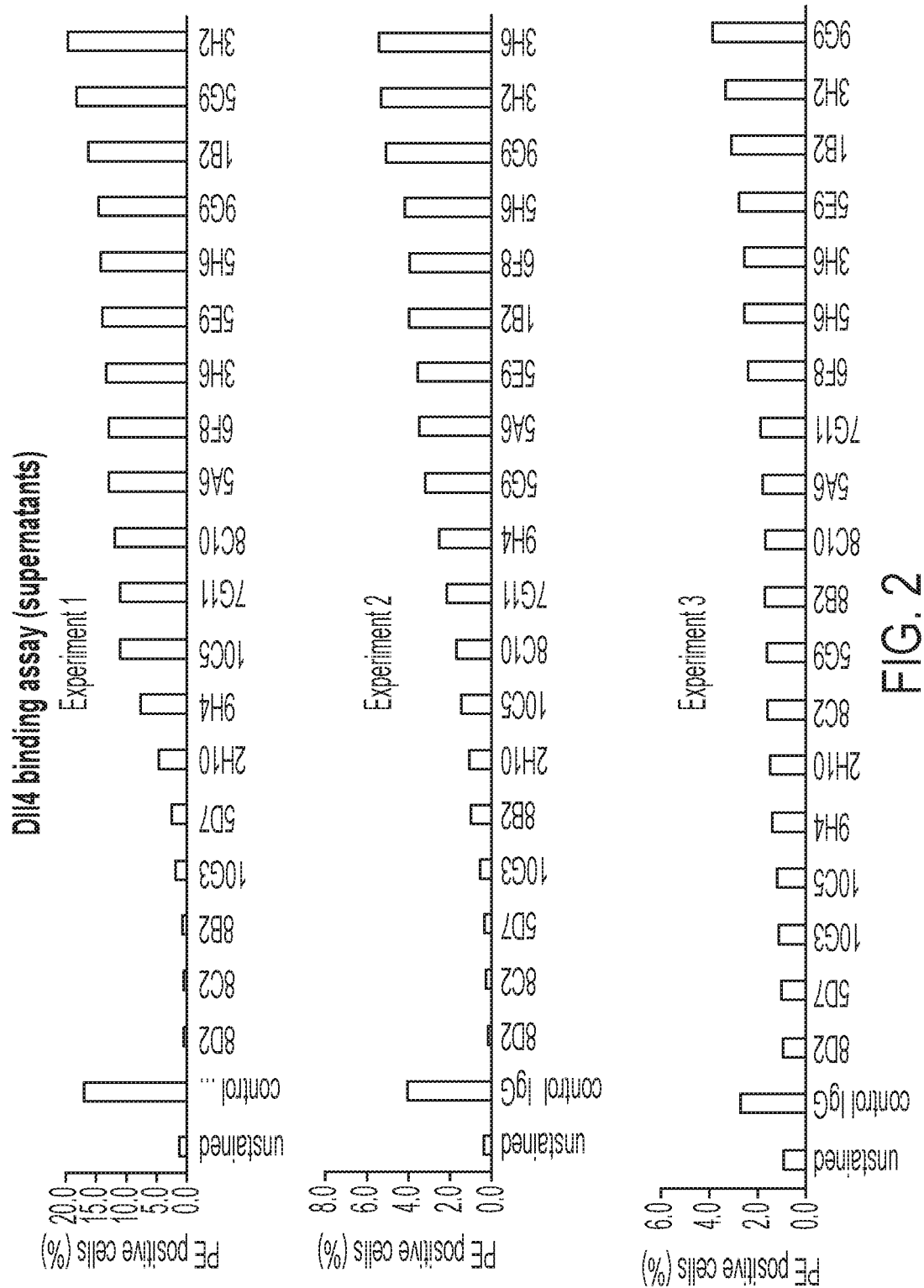
FIG. 2.
Figure 3A:
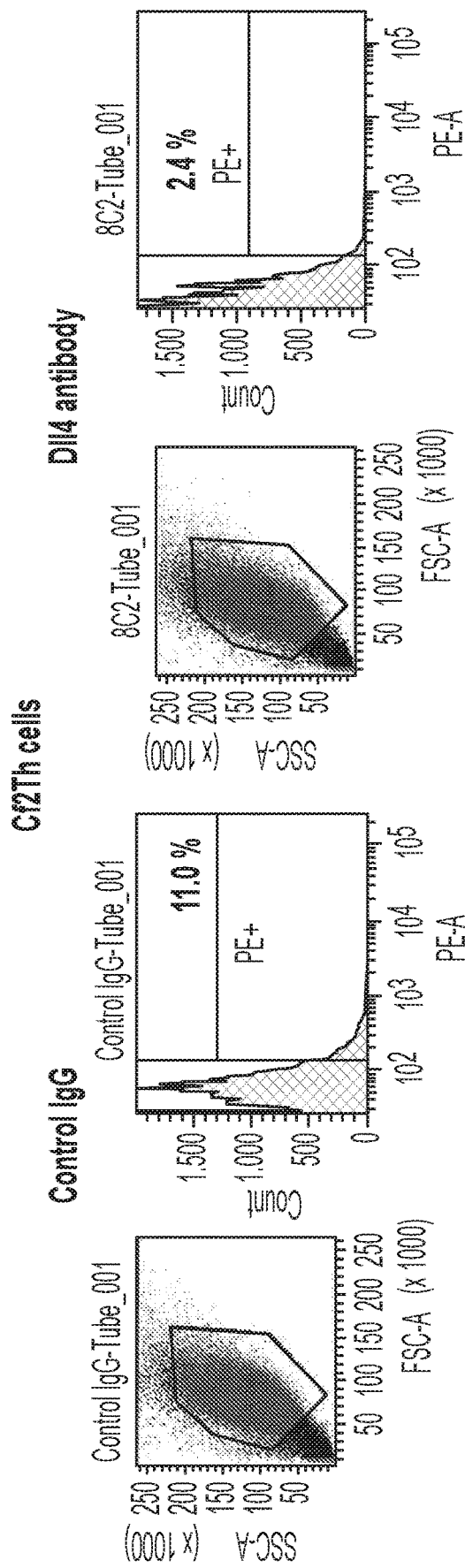
FIGS. 3A and 3B.
Figure 3B:
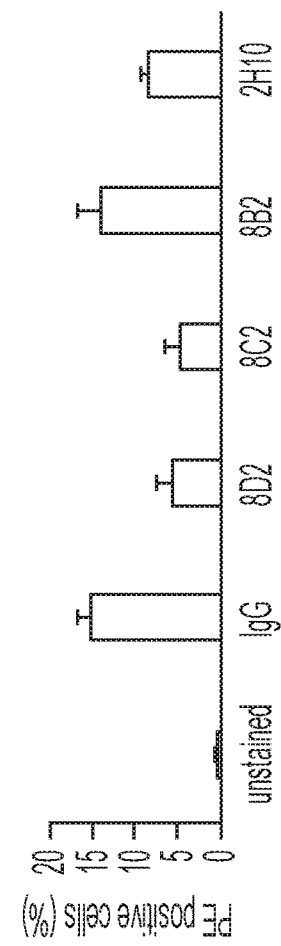
Figure 4A:
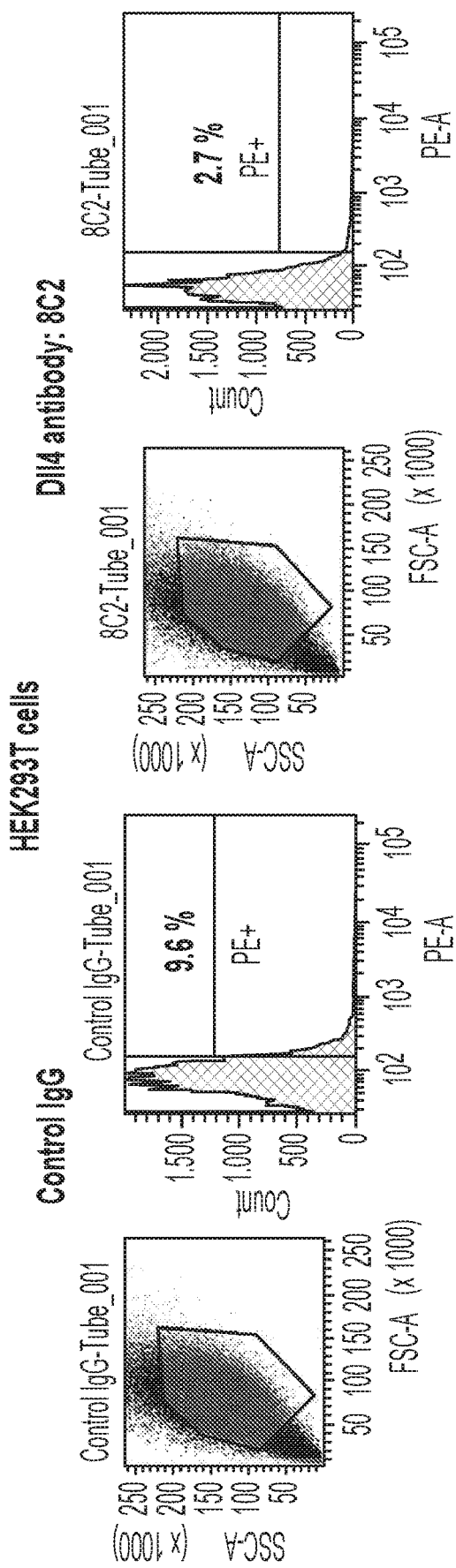
FIGS. 4A and 4B.
Figure 4B:
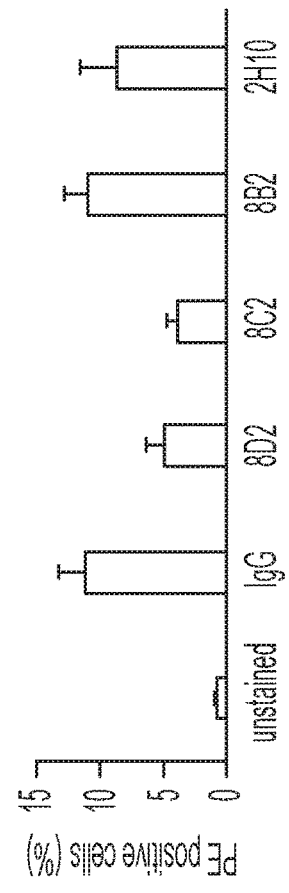
Figure 5:
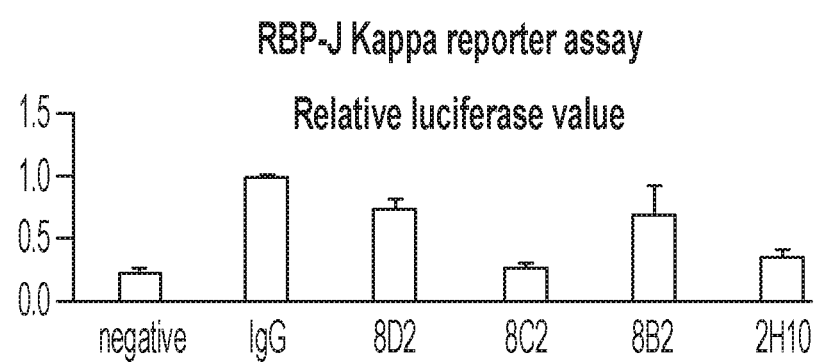
FIG. 5.

Antibody: The term "antibody" as used herein refers to whole antibodies (preferably of the IgG family) that bind to human and or porcine DLL4 and that, when bound, inhibit the binding of DLL4 to NOTCH receptors and the associated NOTCH signaling. Structurally, the intact antibody has two heavy chains and two light chains that are joined together by disulfide bonds. The heavy chains typically each have a constant region (which is divided into CH1, CH2 and CH3 domains) and a variable region which has three hypervariable regions, also called complementarity determining regions (CDRs), that interact directly with DLL4, and that are interspersed with four framework regions (FRs) that are somewhat more conserved. The CDRs and FRs abut one another and are arranged from amino-terminus to carboxy-terminus as: FR1, CDR1, FR2, CDR2, FR3, CDR3, FR4. The light chains have a constant region and a variable region that, like the heavy chain variable region, has three CDRs that interact directly with DLL4 and that are interspersed in the same manner with four framework regions. It is the variable regions of the heavy and light chains that together form a binding site for DLL4. Antibodies or antibody fragments may undergo post translational modifications that are well known in the art including: PEGylation, phosphorylation, methylation, acetylation, ubiquitination, nitrosylation, glycosylation, and lipidation. It will be understood that the invention includes all such routine modifications so long as the antibodies or fragments maintain the ability to bind with specificity to DLL4.

Antibody Fragment: The phrase "antibody fragment," as used herein, refers to one or more portions of an antibody that retain the ability to specifically interact with DLL4 and inhibit it from binding to NOTCH receptors. Examples of binding fragments include, but are not limited to, Fab fragments, Fab2 fragments, and fragments comprising two Fab fragments linked by a disulfide bond.

Isolated antibody: The phrase "isolated antibody," "isolated monoclonal antibody," "isolated antibody fragment" etc. refers to antibodies, fragments etc. that are substantially (at least 90%) free of other antibodies or fragments having different antigenic specificities and substantially free of cellular material.

"Specific binding" or "specificity": As used herein, reference to an antibody that exhibits specific binding or that binds with specificity means that the antibody binds to DLL4 with an equilibrium constant ($K_A$) ($k_{on}/k_{off}$) of at least of at least $1.0 \times 10^4$ $M^{-1}$; and preferably at least $1.0 \times 10^5$ $M^{-1}$; $1.0 \times 10^6$ $M^{-1}$; $1.0 \times 10^7$ $M^{-1}$; $1.0 \times 10^8$ $M^{-1}$; $1.0 \times 10^9$ $M^{-1}$; or $1.0 \times 10^{10}$ $M^{-1}$. Standard assays well known in the art (e.g., ELISAs, Western blots and RIAs) can be used to evaluate the binding of antibodies to DLL4 and the kinetics of binding assessed by, e.g., Biacore analysis, or FACS relative affinity (Scatchard).

Affinity: The term "affinity" refers to the strength of interaction between antibody and antigen. Within each antigenic site, the variable region of the antibody interacts through non-covalent bonds with antigen at numerous sites; the more interactions, the stronger the affinity.

Percent identical: The term percent identical when referring to two or more amino acid or nucleotide sequences refers to, depending on context, the percentage of nucleotides or amino acids that are the same over an entire sequence or a portion of a sequence when the sequences are aligned for maximum correspondence.

Therapeutically effective amount: The term "therapeutically effective amount" refers to a sufficient amount of a DLL4 antibody to prevent the onset, or retard the progression of a disease or condition, symptoms associated with a disease or condition or otherwise result in an improvement in an accepted characteristic of a disease or condition when administered according to a given treatment protocol.

B. The Making of Antibodies

Methods for making the antibodies disclosed herein are described in the Examples section. However, other ways of making antibodies with similar characteristics can be used as well. For example, phage display is a method for making antibodies without using animals.

Also, based on the sequence information disclosed herein, VH/VL encoding nucleotide sequences can be synthesized and cloned into commercial vectors with a mouse/rat/human framework. Recombinant antibodies can then be produced either from a stable cell line or after transient transfection.

C. Drug Formulation

The antibodies or antibody fragments described herein will typically be administered to patients in a pharmaceutical composition comprising the antibody or fragment along with a pharmaceutically acceptable carrier. The carrier may be any solvent, diluent, liquid or solid vehicle that is pharmaceutically acceptable and typically used in formulating drugs. Guidance concerning the making of pharmaceutical formulations can be obtained from standard works in the art (see, e.g., *Remington's Pharmaceutical Sciences, 16th* edition, E. W. Martin, Easton, Pa. (1980)). In addition, pharmaceutical compositions may contain any of the excipients that are commonly used in the art. Examples of carriers or excipients that may be present include, but are not limited to, sugars (e.g., lactose, glucose and sucrose); starches, such as corn starch or potato starch; cellulose and its derivatives (e.g., sodium carboxymethyl cellulose, ethyl cellulose, or cellulose acetate); malt; gelatin; talc; cocoa butter; oils (e.g., peanut oil, cottonseed oil, safflower oil, sesame oil, olive oil, corn oil, or soybean oil); glycols; buffering agents; saline; Ringer's solution; alcohols; lubricants; coloring agents; dispersing agents; coating agents; flavoring agents; preservatives; or antioxidants. Antibody or an antibody fragment may be the sole active ingredient in a composition or other therapeutically active agents may also be present.

The invention is compatible with the delivery of compounds by any route known in the art that permits antibody to remain intact and capable of binding with specificity to DLL4. Options include peroral, internal, rectal, nasal, lingual, transdermal, intravenous, intra-vascular, peri-vascular, intramuscular, intraperitoneal, intracutaneous and subcutaneous routes. The most preferred route is by injection. Injectable preparations may be in the form of sterile, injectable aqueous or oleaginous suspensions, diluents or solvents that may be used may include 1,3-butanediol, water, Ringer's solution and isotonic saline solutions. In addition, oils or fatty acids may be present. Grafts such as autologous vein grafts and tissue-engineered grafts may be treated with the antibody before implantation. Similarly, organs for transplantation may be treated with the antibody before surgery.

Liquid dosage forms for oral administration may include, but are not limited to, pharmaceutically acceptable emulsions, microemulsions, solutions, suspensions, syrups and elixirs. In addition to the active compounds, liquid dosage form may contain inert diluents commonly used in the art, such as, for example, water, or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethyl formamide, oils, glycerol, alcohols, polyethylene glycols, and fatty acid esters.

D. Dosage

Pharmaceutical compositions will typically be given to a patient in one or more unit dosage forms. A "unit dosage form" refers to a single drug administration entity, e.g., a single tablet, capsule or injection volume. The amount of antibody or antibody fragment present should be at least the amount required to reduce the binding of DLL4 at a selected site, for example by at least 10%, or at least 20%, 30%, 40%, 50%, 60% or 70%. On a biological level, sufficient antibody or antibody fragment should be administered in a dosage regimen and over a selected period to show an improvement in one or more clinically accepted measures of a disease or condition or to reduce symptoms associated with the disease or condition. For example, a sufficient amount of an antibody may be administered reduce vein graft rejection 20%, 40%, 60% or more during the first year after the graft is made. The exact dosages given and amount of antibody or antibody fragment in unit dosage forms may be determined for individual patients using methods that are well known in the art of pharmacology and may be further adjusted by physicians based on clinical considerations.

E. Treatment Methods

The antibodies and antibody fragments described herein may be used in treating or preventing any disease or condition associated with the binding of DLL4 to NOTCH receptors. This includes, but is not limited to: cardiovascular disease, including atherogenesis, atherosclerosis and vascular calcification; vein graft disease; arteriovenous fistula failure, nonalcoholic fatty liver disease; obesity; metabolic disease; type 1 and type 2 diabetes; cancer, including colorectal, breast and lung cancer; tumor cell metastasis; and arthritis. The antibodies and antibody fragments described herein may be used in treating or preventing a failure or dysfunction of artificial or tissue-engineered tissues or organs such as artificial vascular grafts and tissue-engineered heart valves; and in preventing rejection or graft-versus-host disease following solid organ and cell transplantation. Subjects, particularly individuals having, or at high risk of developing, one or more such diseases or conditions (e.g., dyslipidemia, diabetes, chronic kidney disease, hypertension) may be treated by administering one or more of the antibodies or antibody fragments described herein. Antibodies or antibody fragments may also be given to test animals, particularly pigs, to study their effect on a disease or condition or the development of a disease or condition. Antibodies or fragments may be administered as the sole active agents in a dosage form, or they may be combined with other drugs to improve overall effectiveness.

F. Use in Immunoassays

As discussed above, the antibodies and antibody fragments of the present invention may be used in the treatment or prevention of a variety of diseases and conditions. In addition, the invention includes immunoassays which use the antibodies or fragments. Procedures that may be used include immunohistochemistry, Western blots (also called immunoblots), procedures involving flow cytometry (e.g., fluorescence-activated cell sorting, "FACS"), chemiluminescence immunoassays, radioimmunoassays (RIAs), enzyme linked immunosorbent assays (ELISAs), "sandwich" immunoassays, immunoprecipitation assays, and immuno-electron microscopy. The antibodies or fragments may be joined to any type of detectable label commonly used in the art, including radioactive labels, fluorophores, chemiluminescent labels, enzymatic labels (e.g., alkaline phosphatase or horseradish peroxidase) and heavy metals.

The assays may be one step (direct) assays, in which the antibodies or fragments are detectably labeled or two step (indirect) assays in which the antibodies or fragments are not themselves labeled but are detected using a second antibody (or other specific binder) that does have a detectable label. There are many variations of these assays that have been described in the art that should be compatible with the present antibodies (see e.g., Wild, David (ed.) (2013), *The Immunoassay Handbook*, 4th edition, Elsevier Science, Hardcover ISBN 9780080970370; Gosling, (2000) *Immunoassays: A Practical Approach* (Practical Approach Series) Oxford Univ Press; Diamandis; Evin, *J. Pept. Sci.* 1(2):132-139 (1995)); Sernee, et al., *Eur. J Biochem.* 270:495-506 (2003); and Pinnix, et al., *J Biol. Chem.* 276:481-487 (2001); each of which is incorporated by reference herein in their entirety).

The assays may be used diagnostically or prognostically to detect and/or quantitate DLL4-expressing cells or a free form of DLL4 in biological samples, including biopsy samples, tissue samples, or samples of bodily fluid such as blood, serum or plasma. Among the diseases or conditions that assays may be used in connection with are: cardiovascular disease, including atherogenesis, atherosclerosis and vascular calcification; vein graft disease, arteriovenous fistula failure; nonalcoholic fatty liver disease; obesity; metabolic disease; type 1 and type 2 diabetes; cancer, including colorectal, breast and lung cancer; tumor cell metastasis; arthritis; failure or dysfunction of artificial or tissue-engineered tissues or organs; and rejection or graft-versus-host disease after organ or cell transplantation. The assays may also be used in research to study DLL4-induced NOTCH activity in cells and test animals.

EXAMPLES

The Making of Antibodies:

cDNAs encoding amino acid 27-529 (ECD) and separately of amino acid 151-221 (DSL domain) of human DLL4 were cloned into separate expression plasmids (Aldevron Freiburg GmbH, Freiburg, Germany). Groups of laboratory rats (Wistar) were immunized with both plasmids by intradermal application of DNA-coated gold-particles using a hand-held device for particle-bombardment ("gene gun"). Cell surface expression on transiently transfected HEK cells was confirmed with anti-tag antibodies recognizing a tag added to the N-terminus of the DLL4 protein. Serum samples were collected after a series of immunizations and tested by flow cytometry on HEK cells transiently transfected with the aforementioned expression plasmids. Antibody-producing cells were isolated and fused with mouse myeloma cells (Ag8) according to standard procedures. Hybridomas producing antibodies specific for DLL4 were identified by screening using human DLL4 ECD, then using pig DLL4 ECD and finally using human DLL1 (negative screening). Cell pellets of positive hybridomas cells were prepared using an RNA protection agent (RNAlater, cat. #AM7020 by ThermoFisher Scientific) and further processed for sequencing of the variable domains of the antibodies.

Example 1: Antibody Binding to DLL4

These experiments examine the binding of monoclonal antibodies 8D2, 8C2 and 2H10 to human DLL4, human DLL1 and porcine DLL4

A. Materials and Methods

Materials

Equipment: Biacore 3000

Assay Buffer-10 mM HEPES buffer (pH 7.4), 150 mM NaCl, 3 mM EDTA, 0.05% P20 (polyoxyethylenesorbitan)

Regeneration Buffer—10 mM Glycine buffer (pH 1.75)

Conjugation Buffer—10 mM sodium acetate buffer (pH 5)

Flow rate—The flow rate used for capturing the ligand is 5 µl/min. The flow rate for kinetics analysis is 30 µl/min.

Abbreviations

| CM5 chip | Carboxymethylated dextran coated chip |
| SPR | Surface Plasmon Resonance |
| RU | Response Units |
| KD | Equilibrium binding affinity constant. KD is defined as the analyte concentration at which 50% of the maximum available ligand is in complex form at equilibrium |
| Analyte | One of the interacting molecules flown over the surface |
| Ligand | One of the interacting molecules immobilized or captured on the surface |
| Rmax | Maximum binding capacity (in RU) of ligand captured/immobilized on the surface |
| MW | Molecular weight |
| HBS-EP | HEPES buffered saline supplemented with EDTA and P20 |
| ka | Association rate constant in $M^{-1}s^{-1}$ |
| kd | Dissociation rate constant in $s^{-1}$ |
| $\chi^2$ | Chi squared |
| EDC | N-ethyl-N'-(3-dimethyl aminopropyl carbodiimide) |
| NHS | N-hydroxy succinamide |

Procedures

Binding experiments were performed on Biacore 3000 at 25° C. Flow cell 2, 3 and 4 of the CM5 chip were coated with the goat anti-rat Fc Capture Ab using EDC/NHS the amine coupling method as per GE manufacturer's instruction. The unoccupied sites were blocked with 1M ethanolamine. Three test antibodies were captured at an RU as indicated on flow cell 2, 3 and 4. Ag was flowed over the chip. Binding of antigen to the antibodies was monitored in real time. From the observed $k_{on}$ and $k_{off}$, KD was determined. For the interactions with fast off rate, steady state kinetics was used to determine KD.

Scouting analysis was performed using a single analyte concentration of 100 nM. At this concentration, binding should be observed even if the ligand binding affinity is weak. Flow cell 1 response was used for reference subtraction.

Full kinetics was performed for control antibody with the range of analyte with a 2 fold serial dilution and flowed over the ligand from lowest to highest concentration range as indicated.

Chi square ($\chi^2$) analysis was carried out between the actual sensorogram (colored line) and the sensorogram generated from the Analysis software (black line) to determine the accuracy of the analysis. $\chi^2$ within 1-2 is considered significant (accurate) and below 1 is highly significant (highly accurate).

B. Results Phase I

Scouting

TABLE E1

| Ligand | Analyte | ka(1/Ms) | kd(1/s) | Rmax (RU) | Conc. Of Analyte | KD(M) | Chi$^2$ |
|---|---|---|---|---|---|---|---|
| BMH-8D2-D10 (220 RU) | Hu.DLL1 | NA | NA | NA | 100 nM | NA | NA |

TABLE E2

| Ligand | Analyte | ka(1/Ms) | kd(1/s) | Rmax (RU) | Conc. Of Analyte | KD(M) | Chi$^2$ |
|---|---|---|---|---|---|---|---|
| BMH-8D2-D10 (220 RU) | Hu.DLL4 | $4.74 \times 10^5$ | $1.08 \times 10^{-3}$ | 117 | 100 nM | $2.27 \times 10^{-9}$ | 6.91 |

TABLE E3

| Ligand | Analyte | ka(1/Ms) | kd(1/s) | Rmax (RU) | Conc. Of Analyte | KD(M) | Chi$^2$ |
|---|---|---|---|---|---|---|---|
| BMH-8C2-D10 (170 RU) | Hu.DLL1 | NA | NA | NA | 100 nM | NA | NA |

TABLE E4

| Ligand | Analyte | ka(1/Ms) | kd(1/s) | Rmax (RU) | Conc. Of Analyte | KD(M) | Chi$^2$ |
|---|---|---|---|---|---|---|---|
| BMH-8C2-D10 (170 RU) | Hu.DLL4 | $1.37 \times 10^5$ | $5.05 \times 10^{-4}$ | 101 | 100 nM | $3.68 \times 10^{-9}$ | 0.0375 |

TABLE E5

| Ligand | Analyte | ka(1/Ms) | kd(1/s) | Rmax (RU) | Conc. Of Analyte | KD(M) | Chi$^2$ |
|---|---|---|---|---|---|---|---|
| BMH-2H10-A7 (161 RU) | Hu.DLL1 | NA | NA | NA | 100 nM | NA | NA |

TABLE E6

| Ligand | Analyte | ka(1/Ms) | kd(1/s) | Rmax (RU) | Conc. Of Analyte | KD(M) | Chi$^2$ |
|---|---|---|---|---|---|---|---|
| BMH-2H10-A7 (161 RU) | Hu.DLL4 | $1.24 \times 10^4$ | $1.09 \times 10^{-3}$ | 30.8 | 100 nM | $8.86 \times 10^{-8}$ | 0.0487 |

TABLE E7

| Ligand | Analyte | ka(1/Ms) | kd(1/s) | Rmax (RU) | Conc. Of Analyte | KD(M) | Chi$^2$ |
|---|---|---|---|---|---|---|---|
| BMH-8D2-D10 (556 RU) | Hu.DLL1 | NA | NA | NA | 1000 nM | NA | NA |

TABLE E8

| Ligand | Analyte | ka(1/Ms) | kd(1/s) | Rmax (RU) | Conc. Of Analyte | KD(M) | Chi$^2$ |
|---|---|---|---|---|---|---|---|
| BMH-8C2-D10 (760 RU) | Hu.DLL1 | NA | NA | NA | 1000 nM | NA | NA |

TABLE E9

| Ligand | Analyte | ka(1/Ms) | kd(1/s) | Rmax (RU) | Conc. Of Analyte | KD(M) | Chi$^2$ |
|---|---|---|---|---|---|---|---|
| BMH-2H10-A7 (522 RU) | Hu.DLL1 | NA | NA | NA | 1000 nM | NA | NA |

TABLE E10

| Ligand | Analyte | ka(1/Ms) | kd(1/s) | Rmax (RU) | Conc. of Analyte (nM) | KD(M) | Chi$^2$ |
|---|---|---|---|---|---|---|---|
| BMH-8D2-D10 (140 RU) | HuDLL4 | $7.59 \times 10^5$ | $1.61 \times 10^{-3}$ | 64.5 | 0<br>0.78<br>1.56<br>3.125<br>6.25<br>12.5<br>12.5 | $2.12 \times 10^{-9}$ | 0.728 |

TABLE E11

| Ligand | Analyte | ka(1/Ms) | kd(1/s) | Rmax (RU) | Conc. Of Analyte (nM) | KD(M) | Chi$^2$ |
|---|---|---|---|---|---|---|---|
| BMH-8C2-D4 (90 RU) | HuDLL4 | $1.28 \times 10^6$ | $4.39 \times 10^{-4}$ | 40.9 | 0<br>1.56<br>3.125<br>6.25<br>12.5<br>25 | $3.43 \times 10^{-10}$ | 0.11 |

TABLE E12

| Ligand | Analyte | ka(1/Ms) | kd(1/s) | Rmax (RU) | Conc. Of Analyte | KD(M) | Chi$^2$ |
|---|---|---|---|---|---|---|---|
| BMH-2H10-A7 (230 RU) | Hu.DLL4 | NA | NA | NA | 0-100 nM | NA | NA |

Conclusions:

Based on the full kinetics, it may be concluded that, among the three antibodies tested, 8D2 and 8C2 were observed to bind very well to human DLL4 In contrast, they failed to bind or weakly bound to human DLL1. Among the two antibodies, 8C2 has about 10-fold higher affinity and also an off rate that is 4 fold lower than 8D2.

C. Results Phase II

Scouting

TABLE E13

| Ligand | Analyte | ka(1/Ms) | kd(1/s) | Rmax (RU) | Conc. Of Analyte | KD(M) | Chi$^2$ |
|---|---|---|---|---|---|---|---|
| BMH-8D2-D10 (80 RU) | Porcine.DLL4 | $1.72 \times 10^5$ | $1.71 \times 10^{-3}$ | 58.7 | 20 nM<br>100 nM | $9.95 \times 10^{-9}$ | 0.713 |

TABLE E14

| Ligand | Analyte | ka(1/Ms) | kd(1/s) | Rmax (RU) | Conc. of Analyte | KD(M) | Chi$^2$ |
|---|---|---|---|---|---|---|---|
| BMH-8C2-D10 (80 RU) | Porcine.DLL4 | $1.06 \times 10^5$ | $1.62 \times 10^{-3}$ | 63.1 | 20 nM<br>100 nM | $1.54 \times 10^{-8}$ | 0.0682 |

TABLE E15

| Ligand | Analyte | ka(1/Ms) | kd(1/s) | Rmax (RU) | Conc. Of Analyte | KD(M) | Chi$^2$ |
|---|---|---|---|---|---|---|---|
| BMH-2H10-A7 (75 RU) | Porcine.DLL4 | $2.79 \times 10^3$ | $3.45 \times 10^{-3}$ | 432 | 20 nM<br>100 nM | $1.24 \times 10^{-6}$ | 0.0937 |

TABLE E16

| Ligand | Analyte | ka(1/Ms) | kd(1/s) | Rmax (RU) | Conc. Of Analyte (nM) | KD(M) | Chi$^2$ |
|---|---|---|---|---|---|---|---|
| BMH-8D2-D10 (110 RU) | Porcine.DLL4 | $2.53 \times 10^5$ | $1.82 \times 10^{-3}$ | 68.1 | 0<br>3.125<br>12.5<br>25<br>50<br>50 | $7.21 \times 10^{-9}$ | 1.22 |

TABLE E17

| Ligand | Analyte | ka(1/Ms) | kd(1/s) | Rmax (RU) | Conc. Of Analyte (nM) | KD(M) | Chi$^2$ |
|---|---|---|---|---|---|---|---|
| BMH-8C2-D10 (80 RU) | Porcine.DLL4 | $2.81 \times 10^5$ | $1.98 \times 10^{-3}$ | 56.7 | 0<br>3.125<br>12.5<br>25<br>50<br>50 | $7.07 \times 10^{-9}$ | 0.652 |

TABLE E18

| Ligand | Analyte | ka(1/Ms) | kd(1/s) | Rmax (RU) | Conc. of Analyte nM | KD(M) | Chi$^2$ |
|---|---|---|---|---|---|---|---|
| BMH-2H10-A7 (130 RU) | Porcine.DLL4 | 295 | $2.76 \times 10^{-3}$ | 3570 | 0<br>25<br>50<br>50<br>100<br>200 | $9.37 \times 10^{-6}$ | 0.369 |

Example 2: Epitope Binding, 8D2 and 8C2 to DLL4

A. Materials and Methods

Materials
 Equipment: Biacore 3000
 Assay Buffer—10 mM HEPES buffer (pH 7.4), 150 mM NaCl, 3 mM FDTA, 0.05% P20 (polyoxyethylenesorbitan)
 Regeneration Buffer—10 mM Glycine buffer (pH 1.75)
 Conjugation Buffer—10 mM sodium acetate buffer (pH 5)
 Flow rate—The flow rate used for capturing the ligand is ta/min. The flow rate for kinetics analysis is 30 μl/min.

Abbreviations

| | |
|---|---|
| CM5 chip | Carboxymethylated dextran coated chip |
| SPR | Surface Plasmon Resonance |
| RU | Response Units |
| KD | Equilibrium binding affinity constant. KD is also defined as the analyte concentration at which 50% of the maximum available ligand is in complex form at equilibrium |
| Analyte | One of the interacting molecules flown over the surface |
| Ligand | One of the interacting molecules immobilized or captured on the surface |
| Rmax | Maximum binding capacity (in RU) of ligand captured/immobilized on the surface |
| MW | Molecular weight |

| | |
|---|---|
| HBS-EP | HEPES buffered saline supplemented with EDTA and P20 |
| ka | Association rate constant in $M^{-1}s^{-1}$ |
| kd | Dissociation rate constant in $s^{-1}$ |
| $\chi^2$ | Chi squared |
| EDC | N-ethyl-N'- (3-dimethyl aminopropyl carbodiimide) |
| NHS | N-hydroxy succinamide |

Procedures

Binding experiments were performed on Biacore 3000 at 25° C. Flow cell 2 and 3 of the CM5 chip were coated with human and porcine DLL4 protein using the EDC/NHS amine coupling method as per GE manufacturer's instructions. The unoccupied sites were blocked with 1M ethanolamine. For epitope binding, 1st rat Ab (8D2) was injected and the binding was visible, then an additional 2 injections were made to completely saturate the binding sites. The second Ab (8C2) was then injected. For the second run, the format was reversed by injecting 8C2 first as above to saturation and then injecting 8D2 as indicated to confirm pairing.

B. Results

Figure 6:
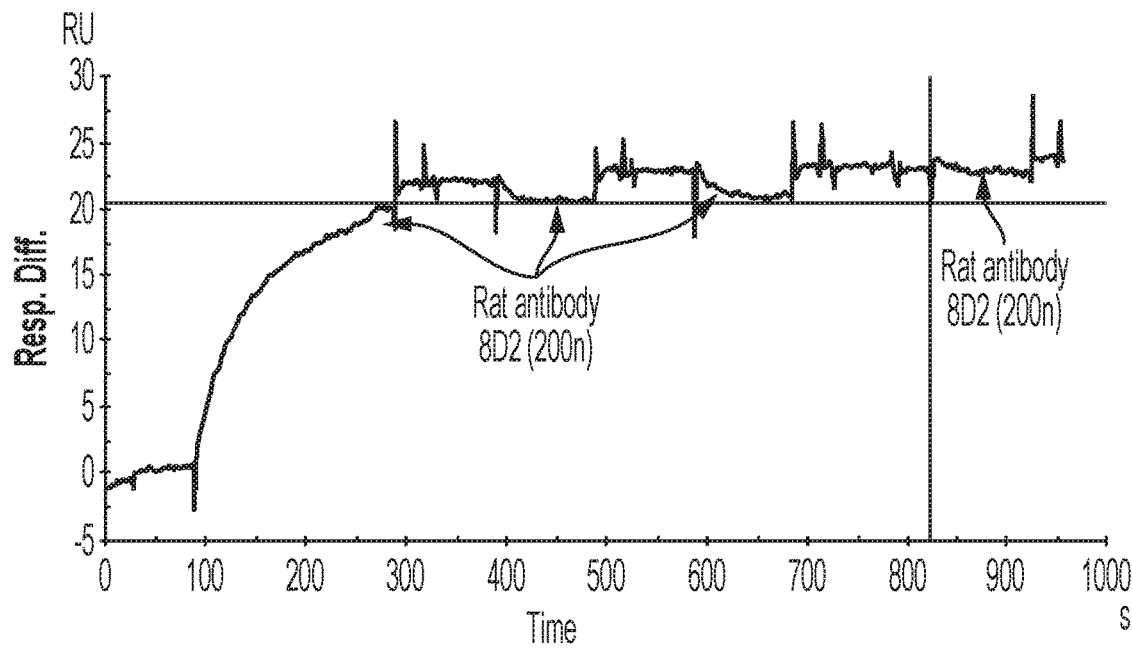
FIG. 6.
Figure 7:
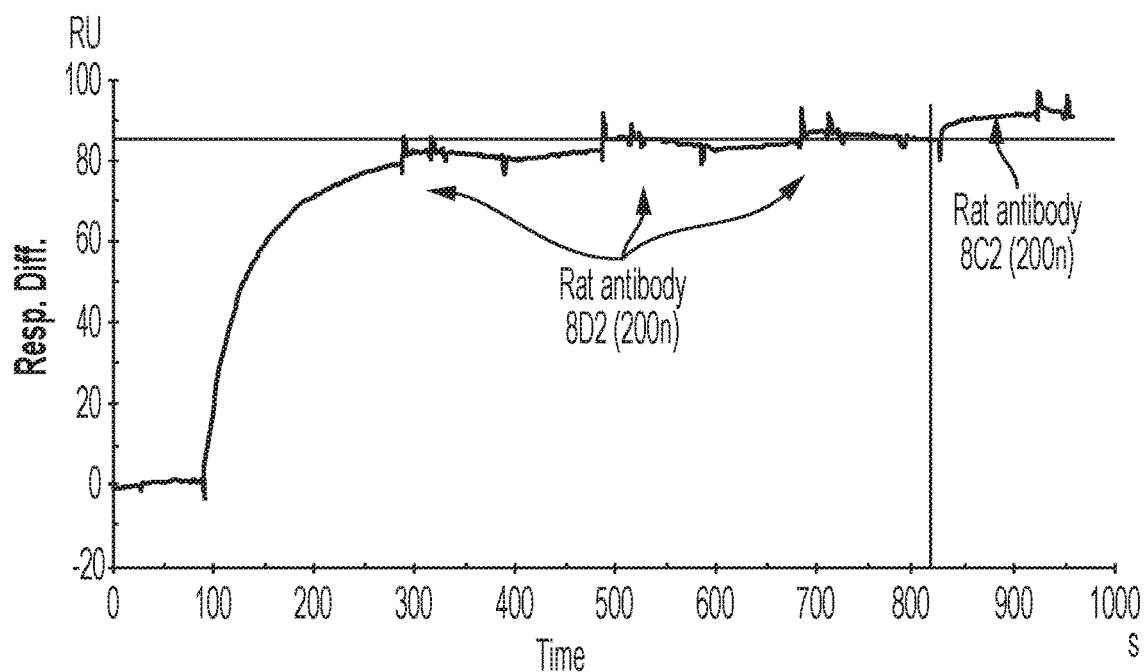
FIG. 7.
Figure 8:
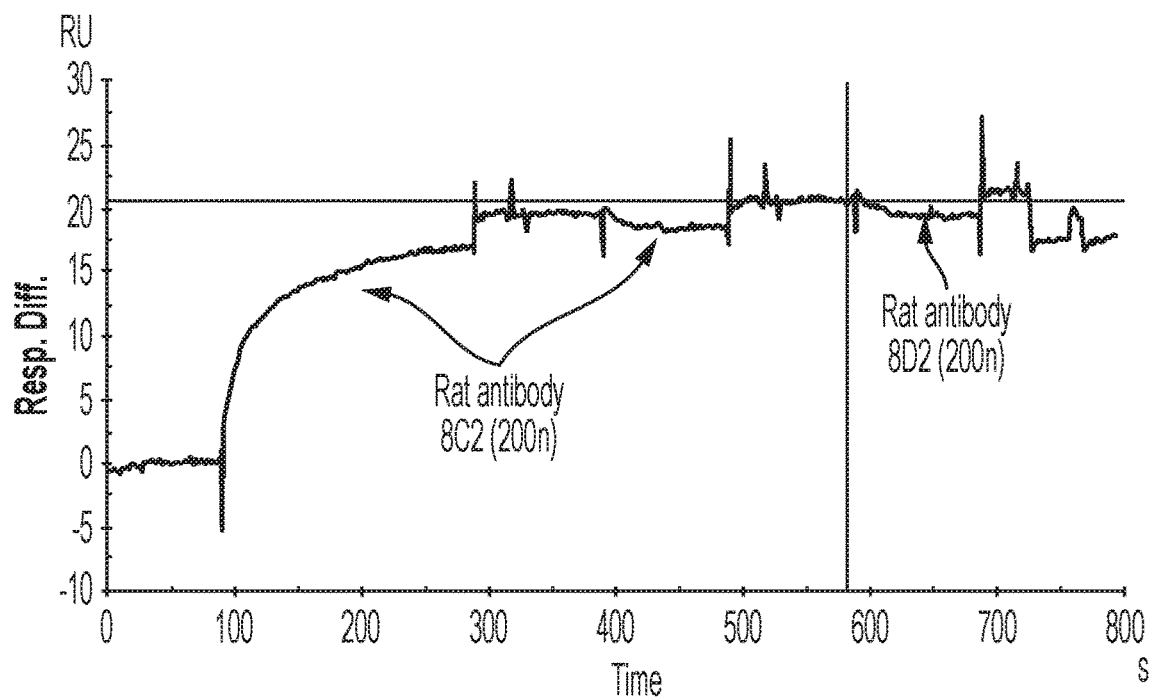
FIG. 8.
Figure 9:
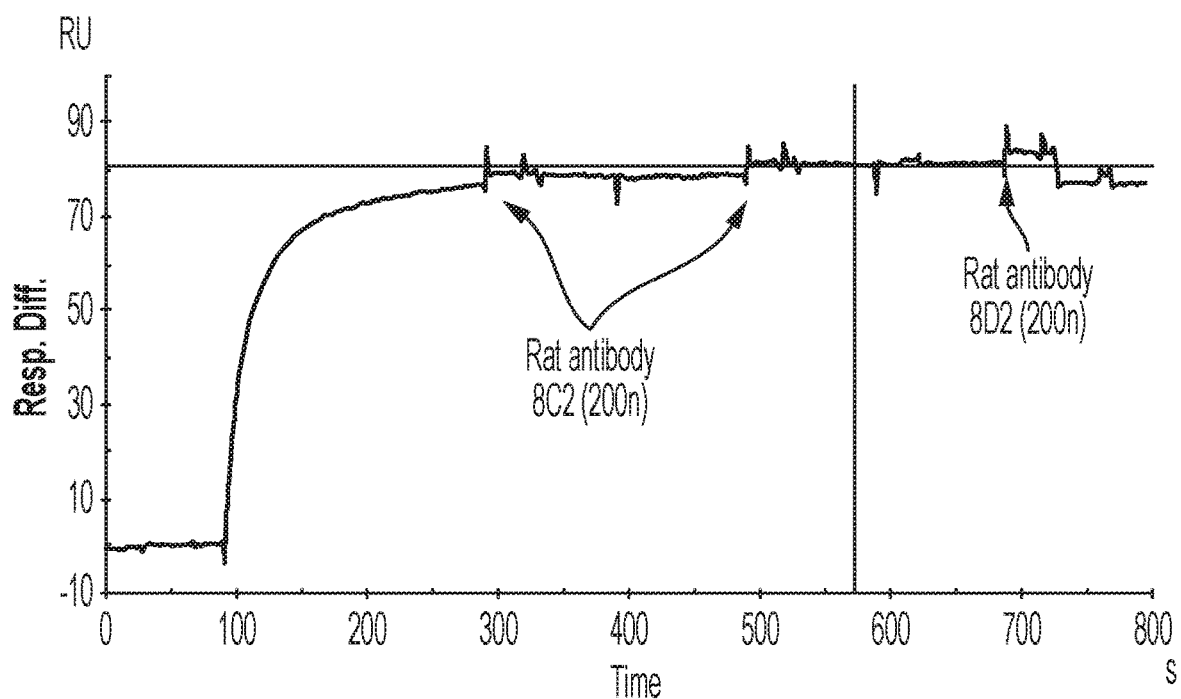
FIG. 9.

Results in which rat 8D2 was bound first to human DLL4, followed by injection of 8C2 are shown in FIG. 6 and results from experiments in which rat 8C2 was bound to human DDL4 first, followed by injection of 8D2 are shown in FIG. 8. Results in which rat 8D2 was bound first to porcine DLL4, followed by injection of rat 8C2 are shown in FIG. 7 and results from experiments in which rat 8C2 was bound to porcine DDL4 first, followed by injection of rat 8D2 are shown in FIG. 9.

C. Conclusions

Based on the observations, it may be concluded that the two antibodies, 8D2 and 8C2, may share the same or an overlapping epitope on both porcine and human DLL4. However, some pairing of the Abs with porcine DLL4 was observed only in one format, where 8D2 injected first and then 8C2. The results failed to show the pairing in the reverse format, where 8C2 injected first to saturation and then 8D2.

Example 3: Sequencing

A. Experimental Design

Overview

The procedure used included standard dye-terminator capillary sequencing of cDNA that was generated from extracted mRNA using an RT-PCR protocol. Proprietary primers were used.

Sequencing Process Overview

Cycle sequencing was performed using BigDye® Terminator v3.1 Cycle Sequencing kits under a standard protocol provided by Life Technologies®. All data was collected using a 3730xl DNA Analyzer system and the Unified Data Collection software provided by Life Technologies® for operation of the 3730xl DNA Analyzer and to collect data produced by the 3730xl DNA Analyzer.

Contig Assembly and Consensus Reporting

Sequence assembly was performed using CodonCode Aligner (CodonCode Corporation). Mixed base calls are resolved by automatically assigning the most prevalent base call to the mixed base calls. Prevalence is determined by both frequency of a base call and the individual quality of the base calls. Observations are reported in the comments section below.

Comments

The heavy chain sequence of antibody 10C5 was not sequenced. 5' RACE resulted in two sequences with similarity to mouse transposing elements.

Due to mis-priming, a shorter amplicon interfered with the sequencing of the heavy chain of antibody 2H10. The desired amplicon was gel extracted and the resulting sequence data was used to resolve mixed base calls.

B. Results

Sequences of the identified antibody variable regions are shown in the attached Sequence Listing.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. An isolated IgG antibody or a fragment thereof that binds to human DLL4 with an affinity at least 1000 times higher than to human DLL1, and which comprises:
   a) a heavy chain variable region at least 90% identical to the amino acid sequence of SEQ ID NO:14 comprising the heavy chain complementarity determining regions (HCDRs) of HCDR1-8C2, HCDR2-8C2, and HCDR3-8C2, wherein HCDR1-8C2 consists of amino acids 31-35 of SEQ ID NO:14; HCDR2-8C2 consists of amino acids 50-65 of SEQ ID NO:14; and HCDR3-8C2 consists of amino acids 96-103 of SEQ ID NO:14; and
   b) a light chain variable region at least 90% identical to the amino acid sequence of SEQ ID NO:16 comprising the light chain complementarity determining regions (LCDRs) of LCDR1-8C2, LCDR2-8C2, and LCDR3-8C2, wherein LCDR1-8C2 consists of amino acids 23-34 of SEQ ID NO:16; LCDR2-8C2 consists of amino acids 50-56 of SEQ ID NO:16; and LCDR3-8C2 consists of amino acids 89-97 of SEQ ID NO:16.

2. The isolated antibody of claim 1, wherein said antibody is a monoclonal antibody.

3. The antibody of claim 1, or the fragment thereof, comprising a ka for human DLL4 of $1.0 \times 10^5 M^{-1}s^{-1}$ or higher.

4. A nucleic acid encoding the antibody of claim 1, wherein the heavy chain variable region is encoded by nucleotides 33-374 of SEQ ID NO:13 and the light chain variable region is encoded by nucleotides 1-318 SEQ ID NO:15.

5. An isolated IgG antibody or a fragment thereof that binds to human DLL4 with an affinity at least 1000 times higher than to human DLL1, and which comprises:
   a) a heavy chain variable region at least 90% identical to the amino acid sequence of SEQ ID NO:18 comprising the HCDRs of HCDR1-8D2, HCDR2-8D2, and HCDR3-8D2, wherein HCDR1-8D2 consists of amino acids 25-29 of SEQ ID NO: 18; HCDR2-8D2 consists of amino acids 44-60 of SEQ ID NO:18; and HCDR3-8D2 consists of amino acids 93-104 of SEQ ID NO: 18; and
   b) a light chain variable region at least 90% identical to amino acid sequence of SEQ ID NO:20 comprising the LCDRs of LCDR1-8D2, LCDR2-8D2, and LCDR3-8D2, wherein LCDR1-8D2 consists of amino acids 23-37 of SEQ ID NO: 20; LCDR2-8D2 consists of amino acids 53-59 of SEQ ID NO:20; and LCDR3-8D2 consists of amino acids 92-100 of SEQ ID NO:20.

6. The isolated antibody of claim 5, wherein said antibody is a monoclonal antibody.

7. The antibody or fragment thereof of claim 5, wherein the heavy chain variable region comprises SEQ ID NO: 18; and the light chain variable region comprises SEQ ID NO:20.

8. The antibody or fragment thereof of claim 5, comprising a ka for human DLL4 of $1.0 \times 10^5 M^{-1}s^{-1}$ or higher.

9. The antibody or the fragment of claim 1, wherein said antibody or fragment comprises a post-translational modification.

10. The antibody or the fragment of claim 9, wherein said post-translational modification is selected from the group consisting of: PEGylation; phosphorylation; methylation; acetylation; ubiquitination; nitrosylation; glycosylation; and lipidation.

11. The antibody or the fragment of claim 1, wherein said antibody or fragment further comprises a detectable label.

12. The antibody or the fragment of claim 11, wherein said detectable label is selected from the group consisting of: a radioactive label; a fluorophore; a chemiluminescent label; an enzymatic label; biotin; avidin; and a heavy metal.

13. The antibody or the fragment of claim 12, wherein said detectable label is an enzyme selected from the group consisting of: alkaline phosphatase and horseradish peroxidase.

14. A method for performing an immunoassay, the method comprising providing a sample, and contacting the sample with the antibody or fragment of claim 1.

15. The method of claim 14, wherein the antibody or fragment further comprises a detectable label.

16. The method of claim 14, wherein the immunoassay further comprises a step of detecting the antibody or fragment by binding a detectably labeled second antibody to the antibody or fragment after it has bound to the sample.

17. A method of detecting or quantitating DLL4-expressing cells in a test sample from a subject, the method comprising contacting the test sample with the antibody or antibody fragment of claim 1, and detecting binding of the antibody or fragment to the sample by binding a detectably labeled second antibody to the antibody or fragment.

18. The method of claim 17, wherein said test sample is a biopsy sample, tissue sample, or a bodily fluid.

19. The method of claim 17, wherein said subject has a disease or condition selected from the group consisting of: cardiovascular disease; vein graft disease; arteriovenous fistula failure; nonalcoholic fatty liver disease; obesity; metabolic disease; type 1 or type 2 diabetes; cancer, and transplanted tissues or organs.

20. An isolated antibody or fragment thereof that binds to human DLL4, comprising:
   a) a heavy chain variable region comprising complementarity-determining regions (CDRs) consisting of amino acids 31-35 of SEQ ID NO:14; amino acids 50-65 of SEQ ID NO: 14; and amino acids 96-103 of SEQ ID NO:14; and
   b) a light chain variable region comprising CDRs consisting of amino acids 23-34 of SEQ ID NO:16; amino acids 50-56 of SEQ ID NO:16; and amino acids 89-97 of SEQ ID NO:16.

21. The isolated antibody or fragment thereof of claim 20, which is an IgG.

22. The isolated antibody of fragment thereof of claim 20, which is humanized.

23. The antibody or fragment thereof of claim 1, wherein the heavy chain variable region comprises SEQ ID NO: 14; and the light chain variable region comprises SEQ ID NO:16.

* * * * *

SEQUENCE LISTING

```
<160> NUMBER OF SEQ ID NOS: 22

<210> SEQ ID NO 1
<211> LENGTH: 483
<212> TYPE: DNA
<213> ORGANISM: Rattus norvegicus
<220> FEATURE:
<221> NAME/KEY: CDS
<222> LOCATION: (31)..(390)
<223> OTHER INFORMATION: Heavy chain variable region of monoclonal
      antibody 2H10
<220> FEATURE:
<221> NAME/KEY: misc_feature
<222> LOCATION: (31)..(120)
<223> OTHER INFORMATION: Codes for heavy chain framework region 1 (HFR1-
      2H10)
<220> FEATURE:
<221> NAME/KEY: misc_feature
<222> LOCATION: (121)..(135)
<223> OTHER INFORMATION: Codes for complementarity determining region 1
```

```
      (HCDR1-2H10)
<220> FEATURE:
<221> NAME/KEY: misc_feature
<222> LOCATION: (136)..(177)
<223> OTHER INFORMATION: Codes for HFR2-2H10
<220> FEATURE:
<221> NAME/KEY: misc_feature
<222> LOCATION: (178)..(225)
<223> OTHER INFORMATION: Codes for HCDR2-2H10
<220> FEATURE:
<221> NAME/KEY: misc_feature
<222> LOCATION: (226)..(321)
<223> OTHER INFORMATION: Codes for HFR3-2H10
<220> FEATURE:
<221> NAME/KEY: misc_feature
<222> LOCATION: (322)..(363)
<223> OTHER INFORMATION: Codes for HCDR3-2H10
<220> FEATURE:
<221> NAME/KEY: misc_feature
<222> LOCATION: (364)..(390)
<223> OTHER INFORMATION: Codes for HFR4-2H10

<400> SEQUENCE: 1
ctggtgacat tccaagctg tgtcctgtcc cag gtg cag gtg aaa gag tca gga          54
                                 Gln Val Gln Val Lys Glu Ser Gly
                                  1               5 cct ggt ctg gtg cag ccc tca cag acc ctg tct ctc acc tgc att gtc         102
Pro Gly Leu Val Gln Pro Ser Gln Thr Leu Ser Leu Thr Cys Ile Val
     10                  15                  20 tct ggg ttc tca cta agc agc tat cat gta agc tgg gtt cgc cag cct         150
Ser Gly Phe Ser Leu Ser Ser Tyr His Val Ser Trp Val Arg Gln Pro
 25                  30                  35                  40 cct gga aag agt ctg gtg tgg atg gga aca ata tgg gct ggt gga ggt         198
Pro Gly Lys Ser Leu Val Trp Met Gly Thr Ile Trp Ala Gly Gly Gly
                 45                  50                  55 aca aat tat aat tcg gct gta caa tcc cga ctg agc atc agc cgg gac         246
Thr Asn Tyr Asn Ser Ala Val Gln Ser Arg Leu Ser Ile Ser Arg Asp
             60                  65                  70 acc tcc aag agc caa gtt ttc tta aaa gtg aac agt ctg caa cct gaa         294
Thr Ser Lys Ser Gln Val Phe Leu Lys Val Asn Ser Leu Gln Pro Glu
         75                  80                  85 gac aca ggc act tac tac tgt gcc aga cat tac tat gat ggt tat tat         342
Asp Thr Gly Thr Tyr Tyr Cys Ala Arg His Tyr Tyr Asp Gly Tyr Tyr
     90                  95                 100 cac ggc ccc tac ttt gat tac tgg ggc caa gga gtc atg gtc aca gtc         390
His Gly Pro Tyr Phe Asp Tyr Trp Gly Gln Gly Val Met Val Thr Val
105                 110                 115                 120 tcctcagccc aaacaacagc cccatctgtc tatccactgg ctcctggatg tggtgataca       450
accagctcca cggtgactct gggatgcctg gtc                                    483

<210> SEQ ID NO 2
<211> LENGTH: 120
<212> TYPE: PRT
<213> ORGANISM: Rattus norvegicus

<400> SEQUENCE: 2

Gln Val Gln Val Lys Glu Ser Gly Pro Gly Leu Val Gln Pro Ser Gln
 1               5                  10                  15

Thr Leu Ser Leu Thr Cys Ile Val Ser Gly Phe Ser Leu Ser Ser Tyr
             20                  25                  30

His Val Ser Trp Val Arg Gln Pro Pro Gly Lys Ser Leu Val Trp Met
         35                  40                  45

Gly Thr Ile Trp Ala Gly Gly Gly Thr Asn Tyr Asn Ser Ala Val Gln
     50                  55                  60
```

```
Ser Arg Leu Ser Ile Ser Arg Asp Thr Ser Lys Ser Gln Val Phe Leu
 65                  70                  75                  80

Lys Val Asn Ser Leu Gln Pro Glu Asp Thr Gly Tyr Tyr Cys Ala
                 85                  90                  95

Arg His Tyr Tyr Asp Gly Tyr Tyr His Gly Pro Tyr Phe Asp Tyr Trp
            100                 105                 110

Gly Gln Gly Val Met Val Thr Val
            115                 120

<210> SEQ ID NO 3
<211> LENGTH: 338
<212> TYPE: DNA
<213> ORGANISM: Rattus norvegicus
<220> FEATURE:
<221> NAME/KEY: CDS
<222> LOCATION: (3)..(311)
<223> OTHER INFORMATION: Light chain variable region of monoclonal
      antibody 2H10
<220> FEATURE:
<221> NAME/KEY: misc_feature
<222> LOCATION: (3)..(53)
<223> OTHER INFORMATION: Codes for light chain framework region 1 (LFR1-
      2H10)
<220> FEATURE:
<221> NAME/KEY: misc_feature
<222> LOCATION: (54)..(86)
<223> OTHER INFORMATION: Codes for light chain complementarity
      determining region 1 (LCDR1-2H10)
<220> FEATURE:
<221> NAME/KEY: misc_feature
<222> LOCATION: (87)..(131)
<223> OTHER INFORMATION: Codes for LFR2-2H10
<220> FEATURE:
<221> NAME/KEY: misc_feature
<222> LOCATION: (132)..(152)
<223> OTHER INFORMATION: Codes for LCDR2-2H10
<220> FEATURE:
<221> NAME/KEY: misc_feature
<222> LOCATION: (153)..(248)
<223> OTHER INFORMATION: Codes for LFR3-2H10
<220> FEATURE:
<221> NAME/KEY: misc_feature
<222> LOCATION: (249)..(275)
<223> OTHER INFORMATION: Codes for LCDR3-2H10
<220> FEATURE:
<221> NAME/KEY: misc_feature
<222> LOCATION: (276)..(311)
<223> OTHER INFORMATION: Codes for LFR4-2H10

<400> SEQUENCE: 3 ag tct cca gct tcc ctg tct gca tct ctg gga gaa act gtc acc ttc      47
   Ser Pro Ala Ser Leu Ser Ala Ser Leu Gly Glu Thr Val Thr Phe
   1               5                  10                  15 gaa tgt cga gca agt gag gac att tac act aat tta gcg tgg tat cag     95
Glu Cys Arg Ala Ser Glu Asp Ile Tyr Thr Asn Leu Ala Trp Tyr Gln
                 20                  25                  30 cag aaa cca ggg aac tct cct cag ctc ctg atc tat gat gca aat acc    143
Gln Lys Pro Gly Asn Ser Pro Gln Leu Leu Ile Tyr Asp Ala Asn Thr
             35                  40                  45 ttg gca gat ggg gtc cca tca cgg ttc agt ggc agt gga tct ggc aca    191
Leu Ala Asp Gly Val Pro Ser Arg Phe Ser Gly Ser Gly Ser Gly Thr
         50                  55                  60 cag ttt tct cta aag att aac agc ctg caa tct gaa gat gtc gcc agt    239
Gln Phe Ser Leu Lys Ile Asn Ser Leu Gln Ser Glu Asp Val Ala Ser
     65                  70                  75 tat ttc tgt caa caa tat gac agt tat ccg tgg acg ttc ggt gga ggc    287
Tyr Phe Cys Gln Gln Tyr Asp Ser Tyr Pro Trp Thr Phe Gly Gly Gly
 80                  85                  90                  95
```

```
acc aag ctg gaa ttg aga cgg gct gatgctgcac caactgtatc catctcc      338
Thr Lys Leu Glu Leu Arg Arg Ala
                100

<210> SEQ ID NO 4
<211> LENGTH: 103
<212> TYPE: PRT
<213> ORGANISM: Rattus norvegicus

<400> SEQUENCE: 4

Ser Pro Ala Ser Leu Ser Ala Ser Leu Gly Glu Thr Val Thr Phe Glu
1               5                   10                  15

Cys Arg Ala Ser Glu Asp Ile Tyr Thr Asn Leu Ala Trp Tyr Gln Gln
                20                  25                  30

Lys Pro Gly Asn Ser Pro Gln Leu Leu Ile Tyr Asp Ala Asn Thr Leu
            35                  40                  45

Ala Asp Gly Val Pro Ser Arg Phe Ser Gly Ser Gly Ser Gly Thr Gln
        50                  55                  60

Phe Ser Leu Lys Ile Asn Ser Leu Gln Ser Glu Asp Val Ala Ser Tyr
65                  70                  75                  80

Phe Cys Gln Gln Tyr Asp Ser Tyr Pro Trp Thr Phe Gly Gly Gly Thr
                85                  90                  95

Lys Leu Glu Leu Arg Arg Ala
            100

<210> SEQ ID NO 5
<211> LENGTH: 485
<212> TYPE: DNA
<213> ORGANISM: Rattus norvegicus
<220> FEATURE:
<221> NAME/KEY: CDS
<222> LOCATION: (55)..(414)
<223> OTHER INFORMATION: Heavy chain variable region for monoclonal
      antibody 5D7
<220> FEATURE:
<221> NAME/KEY: misc_feature
<222> LOCATION: (55)..(144)
<223> OTHER INFORMATION: Codes for heavy chain framework region 1 (HFR1-
      5D7)
<220> FEATURE:
<221> NAME/KEY: misc_feature
<222> LOCATION: (145)..(159)
<223> OTHER INFORMATION: Codes for heavy chain complementarity
      determining region 1 (HCDR1-5D7)
<220> FEATURE:
<221> NAME/KEY: misc_feature
<222> LOCATION: (160)..(201)
<223> OTHER INFORMATION: Codes for HFR2-5D7
<220> FEATURE:
<221> NAME/KEY: misc_feature
<222> LOCATION: (202)..(249)
<223> OTHER INFORMATION: Codes for HCDR2-5D7
<220> FEATURE:
<221> NAME/KEY: misc_feature
<222> LOCATION: (250)..(345)
<223> OTHER INFORMATION: Codes for HFR3-5D7
<220> FEATURE:
<221> NAME/KEY: misc_feature
<222> LOCATION: (346)..(381)
<223> OTHER INFORMATION: Codes for HCDR3-5D7
<220> FEATURE:
<221> NAME/KEY: misc_feature
<222> LOCATION: (382)..(414)
<223> OTHER INFORMATION: Codes for HFR4-5D7

<400> SEQUENCE: 5
aaattcctgg tgctgttgct ctgcctggtg acatttccaa gctgtgtcct gtcc cag    57
                                                            Gln
```

```
gta cag ctg aag gag tca gga cct ggc ctg gtg cag ccc tca gag acc      105
Val Gln Leu Lys Glu Ser Gly Pro Gly Leu Val Gln Pro Ser Glu Thr
         5                  10                  15 ctg tcc ctc acc tgc act gtc tct ggg ttc tca cta acc agg tat gct      153
Leu Ser Leu Thr Cys Thr Val Ser Gly Phe Ser Leu Thr Arg Tyr Ala
             20                  25                  30 gta aac tgg gtt cga cag cct cca gga aaa ggt ctg gag tgg atg gga      201
Val Asn Trp Val Arg Gln Pro Pro Gly Lys Gly Leu Glu Trp Met Gly
     35                  40                  45 aga gtg atg gat gat gga gac aca tca cac aat tca gct ctc aat tcc      249
Arg Val Met Asp Asp Gly Asp Thr Ser His Asn Ser Ala Leu Asn Ser
 50                  55                  60                  65 cga ctg aac atc agc agg gac acc tcc aag aac caa gtt ttc tta aag      297
Arg Leu Asn Ile Ser Arg Asp Thr Ser Lys Asn Gln Val Phe Leu Lys
                 70                  75                  80 atg aac agt ctg caa act gaa gac cca ggc act tat ttc tgt gcc aga      345
Met Asn Ser Leu Gln Thr Glu Asp Pro Gly Thr Tyr Phe Cys Ala Arg
             85                  90                  95 gag gga gat ggt ttt tca tgg tat ggt atg gat gcc tgg ggt caa gga      393
Glu Gly Asp Gly Phe Ser Trp Tyr Gly Met Asp Ala Trp Gly Gln Gly
         100                 105                 110 act tca gtc act gtc tcc tca gcccaaacaa cagccccatc tgtctatcca         444
Thr Ser Val Thr Val Ser Ser
         115                 120 ctggctcctg gatgtggtga tacaaccagc tccacggtga c                        485
```

<210> SEQ ID NO 6
<211> LENGTH: 120
<212> TYPE: PRT
<213> ORGANISM: Rattus norvegicus

<400> SEQUENCE: 6

```
Gln Val Gln Leu Lys Glu Ser Gly Pro Gly Leu Val Gln Pro Ser Glu
1               5                   10                  15

Thr Leu Ser Leu Thr Cys Thr Val Ser Gly Phe Ser Leu Thr Arg Tyr
            20                  25                  30

Ala Val Asn Trp Val Arg Gln Pro Pro Gly Lys Gly Leu Glu Trp Met
        35                  40                  45

Gly Arg Val Met Asp Asp Gly Asp Thr Ser His Asn Ser Ala Leu Asn
    50                  55                  60

Ser Arg Leu Asn Ile Ser Arg Asp Thr Ser Lys Asn Gln Val Phe Leu
65                  70                  75                  80

Lys Met Asn Ser Leu Gln Thr Glu Asp Pro Gly Thr Tyr Phe Cys Ala
                85                  90                  95

Arg Glu Gly Asp Gly Phe Ser Trp Tyr Gly Met Asp Ala Trp Gly Gln
            100                 105                 110

Gly Thr Ser Val Thr Val Ser Ser
        115                 120
```

<210> SEQ ID NO 7
<211> LENGTH: 391
<212> TYPE: DNA
<213> ORGANISM: Rattus norvegicus
<220> FEATURE:
<221> NAME/KEY: CDS
<222> LOCATION: (23)..(352)
<223> OTHER INFORMATION: Light chain variable region for monoclonal
      antibody 5D7
<220> FEATURE:

<221> NAME/KEY: misc_feature
<222> LOCATION: (23)..(88)
<223> OTHER INFORMATION: Codes for light chain framework region 1 (LFR1-5D7)
<220> FEATURE:
<221> NAME/KEY: misc_feature
<222> LOCATION: (89)..(133)
<223> OTHER INFORMATION: Codes for complementarity dtermining region 1 (LCDR1-5D7)
<220> FEATURE:
<221> NAME/KEY: misc_feature
<222> LOCATION: (134)..(178)
<223> OTHER INFORMATION: Codes for LFR2-5D7
<220> FEATURE:
<221> NAME/KEY: misc_feature
<222> LOCATION: (179)..(199)
<223> OTHER INFORMATION: Codes for LCDR2-5D7
<220> FEATURE:
<221> NAME/KEY: misc_feature
<222> LOCATION: (200)..(295)
<223> OTHER INFORMATION: Codes for LFR3-5D7
<220> FEATURE:
<221> NAME/KEY: misc_feature
<222> LOCATION: (296)..(322)
<223> OTHER INFORMATION: Codes for HCDR3-5D7
<220> FEATURE:
<221> NAME/KEY: misc_feature
<222> LOCATION: (323)..(352)
<223> OTHER INFORMATION: Codes for LFR4-5D7

<400> SEQUENCE: 7

```
gtgggttcca gcctccactg gt gac att gtg ctg acc cag tct cct gct ttg        52
                         Asp Ile Val Leu Thr Gln Ser Pro Ala Leu
                          1               5                  10 gct gtg tct cta ggg cag agg gcc aca atc tcc tgt aga gcc agc caa       100
Ala Val Ser Leu Gly Gln Arg Ala Thr Ile Ser Cys Arg Ala Ser Gln
             15                  20                  25 agt gtc agt ata tct agc tat aat ctc atg cag tgg tac caa cag aaa       148
Ser Val Ser Ile Ser Ser Tyr Asn Leu Met Gln Trp Tyr Gln Gln Lys
         30                  35                  40 cca gga cac cag ccc aaa ctc ctc gtc tat gct gca tcc aac ctt gca       196
Pro Gly His Gln Pro Lys Leu Leu Val Tyr Ala Ala Ser Asn Leu Ala
     45                  50                  55 tct ggg atc cct gcc agg ttc agt ggc agt ggg tct ggg aca gac ttc       244
Ser Gly Ile Pro Ala Arg Phe Ser Gly Ser Gly Ser Gly Thr Asp Phe
 60                  65                  70 gcc ctc acc att gat cct gtg cag gct gat gat gtt gca acc tat cac       292
Ala Leu Thr Ile Asp Pro Val Gln Ala Asp Asp Val Ala Thr Tyr His
75                  80                  85                  90 tgt cag cag agt aag gat cat cct ccg acg ttc ggt gga ggc acc aag       340
Cys Gln Gln Ser Lys Asp His Pro Pro Thr Phe Gly Gly Gly Thr Lys
                 95                 100                 105 ctg gaa ttg aaa cgggctgatg ctgcaccaac tgtatccatc tcccaccat            391
Leu Glu Leu Lys
        110
```

<210> SEQ ID NO 8
<211> LENGTH: 110
<212> TYPE: PRT
<213> ORGANISM: Rattus norvegicus

<400> SEQUENCE: 8

```
Asp Ile Val Leu Thr Gln Ser Pro Ala Leu Ala Val Ser Leu Gly Gln
 1               5                  10                  15

Arg Ala Thr Ile Ser Cys Arg Ala Ser Gln Ser Val Ser Ile Ser Ser
             20                  25                  30

Tyr Asn Leu Met Gln Trp Tyr Gln Gln Lys Pro Gly His Gln Pro Lys
```

```
                35                  40                  45
Leu Leu Val Tyr Ala Ala Ser Asn Leu Ala Ser Gly Ile Pro Ala Arg
         50                  55                  60

Phe Ser Gly Ser Gly Ser Gly Thr Asp Phe Ala Leu Thr Ile Asp Pro
 65                  70                  75                  80

Val Gln Ala Asp Asp Val Ala Thr Tyr His Cys Gln Gln Ser Lys Asp
                 85                  90                  95

His Pro Pro Thr Phe Gly Gly Gly Thr Lys Leu Glu Leu Lys
             100                 105                 110
```

<210> SEQ ID NO 9
<211> LENGTH: 436
<212> TYPE: DNA
<213> ORGANISM: Rattus norvegicus
<220> FEATURE:
<221> NAME/KEY: CDS
<222> LOCATION: (1)..(342)
<223> OTHER INFORMATION: Heavy chain variable region for monoclonal
      antibody 8B2
<220> FEATURE:
<221> NAME/KEY: misc_feature
<222> LOCATION: (1)..(57)
<223> OTHER INFORMATION: Codes for heavy chain framework region 1 (HFR1-
      8B2)
<220> FEATURE:
<221> NAME/KEY: misc_feature
<222> LOCATION: (58)..(87)
<223> OTHER INFORMATION: Codes for heavy chain complementarity
      determining region 1 (HCDR1-8B2)
<220> FEATURE:
<221> NAME/KEY: misc_feature
<222> LOCATION: (88)..(129)
<223> OTHER INFORMATION: Codes for HFR2-8B2
<220> FEATURE:
<221> NAME/KEY: misc_feature
<222> LOCATION: (130)..(159)
<223> OTHER INFORMATION: Codes for HCDR2-8B2
<220> FEATURE:
<221> NAME/KEY: misc_feature
<222> LOCATION: (160)..(276)
<223> OTHER INFORMATION: Codes for HFR3-8B2
<220> FEATURE:
<221> NAME/KEY: misc_feature
<222> LOCATION: (277)..(309)
<223> OTHER INFORMATION: Codes for HCDR3-8B2
<220> FEATURE:
<221> NAME/KEY: misc_feature
<222> LOCATION: (310)..(342)
<223> OTHER INFORMATION: Codes for HFR4-8B2

<400> SEQUENCE: 9

```
tct gga gct gag ctg gtg aag cct ggg act tct gtg aag ctg tcc tgc       48
Ser Gly Ala Glu Leu Val Lys Pro Gly Thr Ser Val Lys Leu Ser Cys
  1               5                  10                  15 agg act tct ggc tac acc ttt act aac aac cat atg aac tgg ata aag       96
Arg Thr Ser Gly Tyr Thr Phe Thr Asn Asn His Met Asn Trp Ile Lys
                 20                  25                  30 cag acg act gga cag ggc ctt gag tgg gtt gga att att aat ccg gga      144
Gln Thr Thr Gly Gln Gly Leu Glu Trp Val Gly Ile Ile Asn Pro Gly
             35                  40                  45 agt gga cgt act cac tac aat gtg aag ttc aag ggc aag gcc aca ttg      192
Ser Gly Arg Thr His Tyr Asn Val Lys Phe Lys Gly Lys Ala Thr Leu
         50                  55                  60 act gta gac aaa tcc tcc agc aca gcc ttc atg caa ctc agc agc ctg      240
Thr Val Asp Lys Ser Ser Ser Thr Ala Phe Met Gln Leu Ser Ser Leu
 65                  70                  75                  80 aca cct gag gac tct gcg gtc tat tac tgt gca aga agg ggt gac aac      288
Thr Pro Glu Asp Ser Ala Val Tyr Tyr Cys Ala Arg Arg Gly Asp Asn
```

```
                    85                  90                  95
tct gac tac gct atg gat acc tgg ggt caa gga act tca gtc act gtc    336
Ser Asp Tyr Ala Met Asp Thr Trp Gly Gln Gly Thr Ser Val Thr Val
                   100                 105                 110 tcc tca gcccaaacaa cagccccatc tgtctatcca ctggctcctg gatgtggtga    392
Ser Ser tacaaccagc tccacggtga ctctgggatg cctggtcaag ggct                  436

<210> SEQ ID NO 10
<211> LENGTH: 114
<212> TYPE: PRT
<213> ORGANISM: Rattus norvegicus

<400> SEQUENCE: 10

Ser Gly Ala Glu Leu Val Lys Pro Gly Thr Ser Val Lys Leu Ser Cys
1               5                   10                  15

Arg Thr Ser Gly Tyr Thr Phe Thr Asn Asn His Met Asn Trp Ile Lys
            20                  25                  30

Gln Thr Thr Gly Gln Gly Leu Glu Trp Val Gly Ile Ile Asn Pro Gly
        35                  40                  45

Ser Gly Arg Thr His Tyr Asn Val Lys Phe Lys Gly Lys Ala Thr Leu
    50                  55                  60

Thr Val Asp Lys Ser Ser Ser Thr Ala Phe Met Gln Leu Ser Ser Leu
65                  70                  75                  80

Thr Pro Glu Asp Ser Ala Val Tyr Tyr Cys Ala Arg Arg Gly Asp Asn
                85                  90                  95

Ser Asp Tyr Ala Met Asp Thr Trp Gly Gln Gly Thr Ser Val Thr Val
            100                 105                 110

Ser Ser

<210> SEQ ID NO 11
<211> LENGTH: 488
<212> TYPE: DNA
<213> ORGANISM: Rattus norvegicus
<220> FEATURE:
<221> NAME/KEY: CDS
<222> LOCATION: (141)..(461)
<223> OTHER INFORMATION: Light chain variable region of monoclonal
      antibody 8B2
<220> FEATURE:
<221> NAME/KEY: misc_feature
<222> LOCATION: (141)..(209)
<223> OTHER INFORMATION: Codes for light chain framework region 1 (LFR1-
      8B2)
<220> FEATURE:
<221> NAME/KEY: misc_feature
<222> LOCATION: (210)..(242)
<223> OTHER INFORMATION: Codes for light chain complementarity
      determining region 1 (LCDR1-8B2)
<220> FEATURE:
<221> NAME/KEY: misc_feature
<222> LOCATION: (243)..(287)
<223> OTHER INFORMATION: Codes for LFR2-8B2
<220> FEATURE:
<221> NAME/KEY: misc_feature
<222> LOCATION: (288)..(308)
<223> OTHER INFORMATION: Codes for LCDR2-8B2
<220> FEATURE:
<221> NAME/KEY: misc_feature
<222> LOCATION: (309)..(404)
<223> OTHER INFORMATION: Codes for LFR3-8B2
<220> FEATURE:
<221> NAME/KEY: misc_feature
<222> LOCATION: (405)..(431)
<223> OTHER INFORMATION: Codes for LCDR3-8B2
<220> FEATURE:
```

<221> NAME/KEY: misc_feature
<222> LOCATION: (432)..(461)
<223> OTHER INFORMATION: Codes for LFR4-8B2

<400> SEQUENCE: 11

```
taatacgact cactataggg caagcagtgg tatcaacgca gagtacgggg gaaatgcatc      60
agaccagcat gggcatcaag atggaatcac agactctggt cttcatatcc atactgctct    120
ggttatatgg agctgatggg aac att gta atg acc caa tct ccc aaa tcc atg    173
                      Asn Ile Val Met Thr Gln Ser Pro Lys Ser Met
                        1               5                      10 tcc atg tca gta gga gag agg gtc acc ttg acc tgc aag gcc agt gag      221
Ser Met Ser Val Gly Glu Arg Val Thr Leu Thr Cys Lys Ala Ser Glu
             15                  20                  25 aat gtg gtt act tat gtt tcc tgg tat caa cag aaa cca gag cag tct      269
Asn Val Val Thr Tyr Val Ser Trp Tyr Gln Gln Lys Pro Glu Gln Ser
 30                  35                  40 cct aaa ctg ctg ata tac ggg gca tcc aac cgg tac act ggg gtc ccc      317
Pro Lys Leu Leu Ile Tyr Gly Ala Ser Asn Arg Tyr Thr Gly Val Pro
             45                  50                  55 gat cgc ttc aca ggc agt gga tct gca aca gat ttc act ctg acc atc      365
Asp Arg Phe Thr Gly Ser Gly Ser Ala Thr Asp Phe Thr Leu Thr Ile
 60                  65                  70                  75 agc agt gtg cag gct gaa gac ctt gca gat tat cac tgt gga cag ggt      413
Ser Ser Val Gln Ala Glu Asp Leu Ala Asp Tyr His Cys Gly Gln Gly
             80                  85                  90 tac agc tat ccg tac acg ttc gga ggg ggg acc aag ctg gaa ata aaa      461
Tyr Ser Tyr Pro Tyr Thr Phe Gly Gly Gly Thr Lys Leu Glu Ile Lys
             95                 100                 105 cgggctgatg ctgcaccaac tgtatcc                                         488
```

<210> SEQ ID NO 12
<211> LENGTH: 107
<212> TYPE: PRT
<213> ORGANISM: Rattus norvegicus

<400> SEQUENCE: 12

Asn Ile Val Met Thr Gln Ser Pro Lys Ser Met Ser Met Ser Val Gly
 1               5                  10                  15

Glu Arg Val Thr Leu Thr Cys Lys Ala Ser Glu Asn Val Val Thr Tyr
             20                  25                  30

Val Ser Trp Tyr Gln Gln Lys Pro Glu Gln Ser Pro Lys Leu Leu Ile
         35                  40                  45

Tyr Gly Ala Ser Asn Arg Tyr Thr Gly Val Pro Asp Arg Phe Thr Gly
     50                  55                  60

Ser Gly Ser Ala Thr Asp Phe Thr Leu Thr Ile Ser Ser Val Gln Ala
 65                  70                  75                  80

Glu Asp Leu Ala Asp Tyr His Cys Gly Gln Gly Tyr Ser Tyr Pro Tyr
                 85                  90                  95

Thr Phe Gly Gly Gly Thr Lys Leu Glu Ile Lys
            100                 105

<210> SEQ ID NO 13
<211> LENGTH: 445
<212> TYPE: DNA
<213> ORGANISM: Rattus norvegicus
<220> FEATURE:
<221> NAME/KEY: CDS
<222> LOCATION: (33)..(374)
<223> OTHER INFORMATION: Codes for heavy chain variable region of
      monoclonal antibody 8C2

```
<220> FEATURE:
<221> NAME/KEY: misc_feature
<222> LOCATION: (33)..(122)
<223> OTHER INFORMATION: Codes for heavy chain framework region 1 (HFR1-
      8C2)
<220> FEATURE:
<221> NAME/KEY: misc_feature
<222> LOCATION: (123)..(137)
<223> OTHER INFORMATION: Codes for heavy chain complementarity
      determining region 1 (HCDR1-8C2)
<220> FEATURE:
<221> NAME/KEY: misc_feature
<222> LOCATION: (138)..(179)
<223> OTHER INFORMATION: Codes for HFR2-8C2
<220> FEATURE:
<221> NAME/KEY: misc_feature
<222> LOCATION: (180)..(227)
<223> OTHER INFORMATION: Codes for HCDR2-8C2
<220> FEATURE:
<221> NAME/KEY: misc_feature
<222> LOCATION: (228)..(317)
<223> OTHER INFORMATION: Codes for HFR3-8C2
<220> FEATURE:
<221> NAME/KEY: misc_feature
<222> LOCATION: (318)..(341)
<223> OTHER INFORMATION: Codes for HCDR3-8C2
<220> FEATURE:
<221> NAME/KEY: misc_feature
<222> LOCATION: (342)..(374)
<223> OTHER INFORMATION: Codes for HFR4-8C2

<400> SEQUENCE: 13
gcctggtgac attcccaagc tgtgtcctgt cc cag gtg cag ctg aag gag tca      53
                                    Gln Val Gln Leu Lys Glu Ser
                                     1               5 gga cct ggt ctg gtg cag ccc tca cag acc ctg tcc ctc acc tgc act     101
Gly Pro Gly Leu Val Gln Pro Ser Gln Thr Leu Ser Leu Thr Cys Thr
         10                  15                  20 gtc tct gga atc tca ata agc att tat ggt gtt agc tgg gtt cgc cag     149
Val Ser Gly Ile Ser Ile Ser Ile Tyr Gly Val Ser Trp Val Arg Gln
             25                  30                  35 cct cca gga aag ggt ctg gag tgg atg gga gga ata tgg ggt gat gga     197
Pro Pro Gly Lys Gly Leu Glu Trp Met Gly Gly Ile Trp Gly Asp Gly
 40                  45                  50                  55 tcc aca gat tat aat tca gct ctc aaa tcc cga ctg agc ctc agc agg     245
Ser Thr Asp Tyr Asn Ser Ala Leu Lys Ser Arg Leu Ser Leu Ser Arg
                 60                  65                  70 gac acc tcc aag agc caa gtt ttc tta aaa atg aac agt ctg caa act     293
Asp Thr Ser Lys Ser Gln Val Phe Leu Lys Met Asn Ser Leu Gln Thr
                     75                  80                  85 gaa gac aca gcc att tac ttc tgt acc ctc agt ggg gac ttt gat tac     341
Glu Asp Thr Ala Ile Tyr Phe Cys Thr Leu Ser Gly Asp Phe Asp Tyr
                         90                  95                 100 tgg ggc cac gga gtc ttg gtc aca gtc tcc tca gcccaaacaa cagccccatc   394
Trp Gly His Gly Val Leu Val Thr Val Ser Ser
            105                 110 tgtctatcca ctggctcctg gatgtggtga tacaaccagc tccacggtga c            445

<210> SEQ ID NO 14
<211> LENGTH: 114
<212> TYPE: PRT
<213> ORGANISM: Rattus norvegicus

<400> SEQUENCE: 14

Gln Val Gln Leu Lys Glu Ser Gly Pro Gly Leu Val Gln Pro Ser Gln
 1               5                  10                  15

Thr Leu Ser Leu Thr Cys Thr Val Ser Gly Ile Ser Ile Ser Ile Tyr
```

```
                    20                  25                  30
Gly Val Ser Trp Val Arg Gln Pro Pro Gly Lys Gly Leu Glu Trp Met
            35                  40                  45

Gly Gly Ile Trp Gly Asp Gly Ser Thr Asp Tyr Asn Ser Ala Leu Lys
        50                  55                  60

Ser Arg Leu Ser Leu Ser Arg Asp Thr Ser Lys Ser Gln Val Phe Leu
65                  70                  75                  80

Lys Met Asn Ser Leu Gln Thr Glu Asp Thr Ala Ile Tyr Phe Cys Thr
                85                  90                  95

Leu Ser Gly Asp Phe Asp Tyr Trp Gly His Gly Val Leu Val Thr Val
            100                 105                 110

Ser Ser

<210> SEQ ID NO 15
<211> LENGTH: 349
<212> TYPE: DNA
<213> ORGANISM: Rattus norvegicus
<220> FEATURE:
<221> NAME/KEY: CDS
<222> LOCATION: (1)..(318)
<223> OTHER INFORMATION: Light chain variable region of monoclonal
      antibody 8C2
<220> FEATURE:
<221> NAME/KEY: misc_feature
<222> LOCATION: (1)..(69)
<223> OTHER INFORMATION: Codes for light chain framework region 1 (LFR1-
      8C2)
<220> FEATURE:
<221> NAME/KEY: misc_feature
<222> LOCATION: (70)..(102)
<223> OTHER INFORMATION: Codes for light chain complementarity
      determining region 1 (LCDR1-8C2)
<220> FEATURE:
<221> NAME/KEY: misc_feature
<222> LOCATION: (103)..(147)
<223> OTHER INFORMATION: Codes for LFR2-8C2
<220> FEATURE:
<221> NAME/KEY: misc_feature
<222> LOCATION: (148)..(168)
<223> OTHER INFORMATION: Codes for LCDR2-8C2
<220> FEATURE:
<221> NAME/KEY: misc_feature
<222> LOCATION: (169)..(264)
<223> OTHER INFORMATION: Codes for LFR3-8C2
<220> FEATURE:
<221> NAME/KEY: misc_feature
<222> LOCATION: (265)..(291)
<223> OTHER INFORMATION: Codes for LCDR3-8C2
<220> FEATURE:
<221> NAME/KEY: misc_feature
<222> LOCATION: (292)..(318)
<223> OTHER INFORMATION: Codes for LFR4-8C2

<400> SEQUENCE: 15 gac atc cag ttg acc cag tct cct gcc tcc ctg tct gca tct ctg gat        48
Asp Ile Gln Leu Thr Gln Ser Pro Ala Ser Leu Ser Ala Ser Leu Asp
1               5                   10                  15 gaa att gtc acc atc aca tgc cag gca agc ctg gac att ggt aat tgg        96
Glu Ile Val Thr Ile Thr Cys Gln Ala Ser Leu Asp Ile Gly Asn Trp
                20                  25                  30 tta gca tgg tat cag cag aaa aca ggg aaa tct cct caa ctc ctg atc      144
Leu Ala Trp Tyr Gln Gln Lys Thr Gly Lys Ser Pro Gln Leu Leu Ile
            35                  40                  45 tat ggt gca acc agc ttg gcg ggt ggg gtc cca tca agg ttc agc ggc      192
Tyr Gly Ala Thr Ser Leu Ala Gly Gly Val Pro Ser Arg Phe Ser Gly
        50                  55                  60 agt aga tct ggc aca cag tat tct ctt aag atc agc aaa cta cag gtt      240
```

```
Ser Arg Ser Gly Thr Gln Tyr Ser Leu Lys Ile Ser Lys Leu Gln Val
 65                  70                  75                  80 gaa gat act gga atc tat tac tgt cta cag cat tat cgt gct cca ttc      288
Glu Asp Thr Gly Ile Tyr Tyr Cys Leu Gln His Tyr Arg Ala Pro Phe
                     85                  90                  95 acg ttc ggc tca ggg acg aag ttg gaa ata aaacgggctg atgctgcacc        338
Thr Phe Gly Ser Gly Thr Lys Leu Glu Ile
            100                 105 aactgtatcc a                                                          349

<210> SEQ ID NO 16
<211> LENGTH: 106
<212> TYPE: PRT
<213> ORGANISM: Rattus norvegicus

<400> SEQUENCE: 16

Asp Ile Gln Leu Thr Gln Ser Pro Ala Ser Leu Ser Ala Ser Leu Asp
 1               5                  10                  15

Glu Ile Val Thr Ile Thr Cys Gln Ala Ser Leu Asp Ile Gly Asn Trp
             20                  25                  30

Leu Ala Trp Tyr Gln Gln Lys Thr Gly Lys Ser Pro Gln Leu Leu Ile
         35                  40                  45

Tyr Gly Ala Thr Ser Leu Ala Gly Gly Val Pro Ser Arg Phe Ser Gly
     50                  55                  60

Ser Arg Ser Gly Thr Gln Tyr Ser Leu Lys Ile Ser Lys Leu Gln Val
 65                  70                  75                  80

Glu Asp Thr Gly Ile Tyr Tyr Cys Leu Gln His Tyr Arg Ala Pro Phe
                     85                  90                  95

Thr Phe Gly Ser Gly Thr Lys Leu Glu Ile
            100                 105

<210> SEQ ID NO 17
<211> LENGTH: 438
<212> TYPE: DNA
<213> ORGANISM: Rattus norvegicus
<220> FEATURE:
<221> NAME/KEY: CDS
<222> LOCATION: (1)..(345)
<223> OTHER INFORMATION: Heavy chain variable region for monoclonal
      antibody 8D2
<220> FEATURE:
<221> NAME/KEY: misc_feature
<222> LOCATION: (1)..(72)
<223> OTHER INFORMATION: Codes for heavy chain framework region 1 (HFR1-
      8D2)
<220> FEATURE:
<221> NAME/KEY: misc_feature
<222> LOCATION: (73)..(87)
<223> OTHER INFORMATION: Codes for heavy chain complementarity
      determining region 1 (HCDR1-8D2)
<220> FEATURE:
<221> NAME/KEY: misc_feature
<222> LOCATION: (88)..(129)
<223> OTHER INFORMATION: Codes for HFR2-8D2
<220> FEATURE:
<221> NAME/KEY: misc_feature
<222> LOCATION: (130)..(180)
<223> OTHER INFORMATION: Codes for HCDR2-8D2
<220> FEATURE:
<221> NAME/KEY: misc_feature
<222> LOCATION: (181)..(276)
<223> OTHER INFORMATION: Codes for HFR3-8D2
<220> FEATURE:
<221> NAME/KEY: misc_feature
<222> LOCATION: (277)..(312)
<223> OTHER INFORMATION: Codes for HCDR3-8D2
<220> FEATURE:
```

<221> NAME/KEY: misc_feature
<222> LOCATION: (313)..(345)
<223> OTHER INFORMATION: Codes for HFR4-8D2

<400> SEQUENCE: 17

```
tct ggg gga ggc tta gtg cag cct gga agg tcc atg aag ctc tcc tgt      48
Ser Gly Gly Gly Leu Val Gln Pro Gly Arg Ser Met Lys Leu Ser Cys
1               5                   10                  15 gca gcc tca gga ttc act ttc agt aac tat gac atg gcc tgg gtc cgc      96
Ala Ala Ser Gly Phe Thr Phe Ser Asn Tyr Asp Met Ala Trp Val Arg
            20                  25                  30 cag gat cca aag aag ggt ctg gaa tgg gtc gca aca atc agt tat gat     144
Gln Asp Pro Lys Lys Gly Leu Glu Trp Val Ala Thr Ile Ser Tyr Asp
        35                  40                  45 ggt aga agc act tac tat cga gac tcc gtg aag ggc cga ttc act att     192
Gly Arg Ser Thr Tyr Tyr Arg Asp Ser Val Lys Gly Arg Phe Thr Ile
    50                  55                  60 tcc aga gat aat gca aaa agt acc cta tat ctg caa atg gac agt ctg     240
Ser Arg Asp Asn Ala Lys Ser Thr Leu Tyr Leu Gln Met Asp Ser Leu
65                  70                  75                  80 agg tct gag gac acg gcc act tat tac tgt aag gac tat gat ggg cat     288
Arg Ser Glu Asp Thr Ala Thr Tyr Tyr Cys Lys Asp Tyr Asp Gly His
                85                  90                  95 tat cac ccc tat ggt atg gag gcc tgg ggt caa gga att tca gtc act     336
Tyr His Pro Tyr Gly Met Glu Ala Trp Gly Gln Gly Ile Ser Val Thr
            100                 105                 110 gtc tcc tca gcccaaacaa cagccccatc tgtctatcca ctggctcctg             385
Val Ser Ser
        115 gatgtggtga tacaaccagc tccacggtga ctctgggatg cctggtcaag ggc           438
```

<210> SEQ ID NO 18
<211> LENGTH: 115
<212> TYPE: PRT
<213> ORGANISM: Rattus norvegicus

<400> SEQUENCE: 18

```
Ser Gly Gly Gly Leu Val Gln Pro Gly Arg Ser Met Lys Leu Ser Cys
1               5                   10                  15

Ala Ala Ser Gly Phe Thr Phe Ser Asn Tyr Asp Met Ala Trp Val Arg
            20                  25                  30

Gln Asp Pro Lys Lys Gly Leu Glu Trp Val Ala Thr Ile Ser Tyr Asp
        35                  40                  45

Gly Arg Ser Thr Tyr Tyr Arg Asp Ser Val Lys Gly Arg Phe Thr Ile
    50                  55                  60

Ser Arg Asp Asn Ala Lys Ser Thr Leu Tyr Leu Gln Met Asp Ser Leu
65                  70                  75                  80

Arg Ser Glu Asp Thr Ala Thr Tyr Tyr Cys Lys Asp Tyr Asp Gly His
                85                  90                  95

Tyr His Pro Tyr Gly Met Glu Ala Trp Gly Gln Gly Ile Ser Val Thr
            100                 105                 110

Val Ser Ser
        115
```

<210> SEQ ID NO 19
<211> LENGTH: 402
<212> TYPE: DNA
<213> ORGANISM: Rattus norvegicus
<220> FEATURE:
<221> NAME/KEY: CDS

```
<222> LOCATION: (36)..(365)
<223> OTHER INFORMATION: Light chain variable region of monoclonal
      antibody 8D2
<220> FEATURE:
<221> NAME/KEY: misc_feature
<222> LOCATION: (36)..(101)
<223> OTHER INFORMATION: Codes for light chain framework region 1 (LFR1-
      8D2)
<220> FEATURE:
<221> NAME/KEY: misc_feature
<222> LOCATION: (102)..(146)
<223> OTHER INFORMATION: Codes for light chain complementarity region 1
      (LCDR1-8D2)
<220> FEATURE:
<221> NAME/KEY: misc_feature
<222> LOCATION: (147)..(191)
<223> OTHER INFORMATION: Codes for LFR2-8D2
<220> FEATURE:
<221> NAME/KEY: misc_feature
<222> LOCATION: (192)..(212)
<223> OTHER INFORMATION: Codes for LCDR2-8D2
<220> FEATURE:
<221> NAME/KEY: misc_feature
<222> LOCATION: (213)..(308)
<223> OTHER INFORMATION: Codes for LFR3-8D2
<220> FEATURE:
<221> NAME/KEY: misc_feature
<222> LOCATION: (309)..(335)
<223> OTHER INFORMATION: Codes for LCDR3-8D2
<220> FEATURE:
<221> NAME/KEY: misc_feature
<222> LOCATION: (336)..(365)
<223> OTHER INFORMATION: Codes for LFR4-8D2

<400> SEQUENCE: 19
ggttgctgct gctgtgggtt ccaggctcca ctggt gac att gtg ctg acc cag         53
                                        Asp Ile Val Leu Thr Gln
                                         1               5 tct cct gct ttg gct gtg act cta ggg cag agg gcc aca atc tcc tgt        101
Ser Pro Ala Leu Ala Val Thr Leu Gly Gln Arg Ala Thr Ile Ser Cys
         10                  15                  20 aga gcc agc cag agt gtc act ata tct aac tat aat ctc atg cag tgg        149
Arg Ala Ser Gln Ser Val Thr Ile Ser Asn Tyr Asn Leu Met Gln Trp
             25                  30                  35 tac caa cag aga cca gga cgg caa ccc aaa ctc ctc atc tat gat gca        197
Tyr Gln Gln Arg Pro Gly Arg Gln Pro Lys Leu Leu Ile Tyr Asp Ala
         40                  45                  50 tcc aac cta gca tct ggg atc cct gcc agg ttc agt ggc agt ggg tct        245
Ser Asn Leu Ala Ser Gly Ile Pro Ala Arg Phe Ser Gly Ser Gly Ser
 55                  60                  65                  70 ggg aca gac ttc acc ctc acc att gat cct gtg cag gct gat gat att        293
Gly Thr Asp Phe Thr Leu Thr Ile Asp Pro Val Gln Ala Asp Asp Ile
                 75                  80                  85 gca acc tat tac tgt cag cag agt agg gat gat cct cgg acg ttc ggt        341
Ala Thr Tyr Tyr Cys Gln Gln Ser Arg Asp Asp Pro Arg Thr Phe Gly
             90                  95                 100 gga ggc acc aag ctg gaa ttg aga cgggctgatg ctgcaccaac tgtatccatc       395
Gly Gly Thr Lys Leu Glu Leu Arg
         105                 110 tcccacc                                                                402

<210> SEQ ID NO 20
<211> LENGTH: 110
<212> TYPE: PRT
<213> ORGANISM: Rattus norvegicus

<400> SEQUENCE: 20

Asp Ile Val Leu Thr Gln Ser Pro Ala Leu Ala Val Thr Leu Gly Gln
```

```
                1               5                      10                      15
              Arg Ala Thr Ile Ser Cys Arg Ala Ser Gln Ser Val Thr Ile Ser Asn
                             20                      25                      30

Tyr Asn Leu Met Gln Trp Tyr Gln Gln Arg Pro Gly Arg Gln Pro Lys
                         35                      40                      45

Leu Leu Ile Tyr Asp Ala Ser Asn Leu Ala Ser Gly Ile Pro Ala Arg
                       50                      55                      60

Phe Ser Gly Ser Gly Ser Gly Thr Asp Phe Thr Leu Thr Ile Asp Pro
              65                      70                      75                      80

Val Gln Ala Asp Asp Ile Ala Thr Tyr Tyr Cys Gln Gln Ser Arg Asp
                                  85                      90                      95

Asp Pro Arg Thr Phe Gly Gly Gly Thr Lys Leu Glu Leu Arg
                             100                     105                     110

<210> SEQ ID NO 21
<211> LENGTH: 333
<212> TYPE: DNA
<213> ORGANISM: Rattus norvegicus
<220> FEATURE:
<221> NAME/KEY: CDS
<222> LOCATION: (1)..(306)
<223> OTHER INFORMATION: Light chain variable region of monoclonal
      antibody 10C5
<220> FEATURE:
<221> NAME/KEY: misc_feature
<222> LOCATION: (1)..(54)
<223> OTHER INFORMATION: Codes for light chain framework region 1 (LFR1-
      10C5)
<220> FEATURE:
<221> NAME/KEY: misc_feature
<222> LOCATION: (55)..(87)
<223> OTHER INFORMATION: Codes for light chain complementarity
      determining region 1 (LCDR1-10C5)
<220> FEATURE:
<221> NAME/KEY: misc_feature
<222> LOCATION: (88)..(132)
<223> OTHER INFORMATION: Codes for LFR2-10C5
<220> FEATURE:
<221> NAME/KEY: misc_feature
<222> LOCATION: (133)..(153)
<223> OTHER INFORMATION: Codes for LCDR2-10C5
<220> FEATURE:
<221> NAME/KEY: misc_feature
<222> LOCATION: (154)..(249)
<223> OTHER INFORMATION: Codes for LFR3-10C5
<220> FEATURE:
<221> NAME/KEY: misc_feature
<222> LOCATION: (250)..(276)
<223> OTHER INFORMATION: Codes for LCDR3-10C5
<220> FEATURE:
<221> NAME/KEY: misc_feature
<222> LOCATION: (277)..(306)
<223> OTHER INFORMATION: Codes for LFR4-10C5

<400> SEQUENCE: 21 cag tct cct gcc tcc ctg tct gca tct ctg gaa gaa att gtc acc atc        48
Gln Ser Pro Ala Ser Leu Ser Ala Ser Leu Glu Glu Ile Val Thr Ile
1               5                      10                      15 aca tgc cag gca agc cag gac att ggt aat tgg tta tca tgg tat cag        96
Thr Cys Gln Ala Ser Gln Asp Ile Gly Asn Trp Leu Ser Trp Tyr Gln
                   20                      25                      30 cag aaa cca ggg aaa tct cct cag ctc ctg atc tat ggt gca acc agc       144
Gln Lys Pro Gly Lys Ser Pro Gln Leu Leu Ile Tyr Gly Ala Thr Ser
               35                      40                      45 ttg gca gat ggg gtc cca tca agg ttc agc ggc agt aga tct ggc aca       192
Leu Ala Asp Gly Val Pro Ser Arg Phe Ser Gly Ser Arg Ser Gly Thr
           50                      55                      60
```

```
cag tat tct ctt aag atc agc aga cta cag gtt gaa gat att gga atc    240
Gln Tyr Ser Leu Lys Ile Ser Arg Leu Gln Val Glu Asp Ile Gly Ile
65              70                  75                  80 tat tac tgt cta cag gct tat agt gct cct cgg acg ttc ggt gga ggc    288
Tyr Tyr Cys Leu Gln Ala Tyr Ser Ala Pro Arg Thr Phe Gly Gly Gly
                85                  90                  95 acc aag ctg gaa ttg aaa cgggctgatg ctgcaccaac tgtatcc              333
Thr Lys Leu Glu Leu Lys
            100

<210> SEQ ID NO 22
<211> LENGTH: 102
<212> TYPE: PRT
<213> ORGANISM: Rattus norvegicus

<400> SEQUENCE: 22

Gln Ser Pro Ala Ser Leu Ser Ala Ser Leu Glu Glu Ile Val Thr Ile
1               5                   10                  15

Thr Cys Gln Ala Ser Gln Asp Ile Gly Asn Trp Leu Ser Trp Tyr Gln
                20                  25                  30

Gln Lys Pro Gly Lys Ser Pro Gln Leu Leu Ile Tyr Gly Ala Thr Ser
            35                  40                  45

Leu Ala Asp Gly Val Pro Ser Arg Phe Ser Gly Ser Arg Ser Gly Thr
        50                  55                  60

Gln Tyr Ser Leu Lys Ile Ser Arg Leu Gln Val Glu Asp Ile Gly Ile
65              70                  75                  80

Tyr Tyr Cys Leu Gln Ala Tyr Ser Ala Pro Arg Thr Phe Gly Gly Gly
                85                  90                  95

Thr Lys Leu Glu Leu Lys
            100
```